(12) United States Patent
Nassif

(10) Patent No.: US 10,850,104 B2
(45) Date of Patent: Dec. 1, 2020

(54) IMPLANTABLE NERVE STIMULATOR HAVING INTERNAL ELECTRONICS WITHOUT ASIC AND METHODS OF USE

(71) Applicant: Axonics Modulation Technologies, Inc., Irvine, CA (US)

(72) Inventor: Rabih Nassif, Santa Ana, CA (US)

(73) Assignee: AXONICS MODULATION TECHNOLOGIES, INC., Irvine, CA (US)

( * ) Notice: Subject to any disclaimer, the term of this patent is extended or adjusted under 35 U.S.C. 154(b) by 86 days.

(21) Appl. No.: 15/889,844

(22) Filed: Feb. 6, 2018

(65) Prior Publication Data

US 2018/0333581 A1    Nov. 22, 2018

Related U.S. Application Data

(60) Division of application No. 15/414,531, filed on Jan. 24, 2017, now Pat. No. 9,925,381, which is a
(Continued)

(51) Int. Cl.
*A61N 1/36* (2006.01)
*A61N 1/05* (2006.01)
(Continued)

(52) U.S. Cl.
CPC ....... *A61N 1/36125* (2013.01); *A61N 1/0551* (2013.01); *A61N 1/36007* (2013.01); *A61N 1/3787* (2013.01); *A61N 1/3754* (2013.01)

(58) Field of Classification Search
CPC ............ A61B 2560/0468; A61B 5/486; A61B 2562/02; A61B 5/4836; A61N 1/36125;
(Continued)

(56) References Cited

U.S. PATENT DOCUMENTS 3,057,356 A    10/1962    Greatbatch
3,348,548 A    10/1967    Chardack
(Continued)

FOREIGN PATENT DOCUMENTS

AT    520440    9/2011
AU    4664800    11/2000
(Continued)

OTHER PUBLICATIONS

US 9,601,939 B2, 03/2017, Cong et al. (withdrawn)
(Continued)

*Primary Examiner* — Deborah L Malamud
(74) *Attorney, Agent, or Firm* — Kilpatrick Townsend & Stockton LLP

(57) ABSTRACT

An implantable pulse generator that includes a current source/sink generator is disclosed herein. The current source/sink generator includes a current drive differential amplifier. The current driver differential amplifier is configured to selectively source current to, or sink current from a target tissue. The current drive differential amplifier includes an inverting input and a non-inverting input. One of the inputs of the current drive differential amplifier is connected to a virtual ground, and the other is connected to a current command. A stimulation controller can supply a voltage to the other of the inputs of the current drive differential amplifier to select either current sourcing or current sinking.

21 Claims, 13 Drawing Sheets

Related U.S. Application Data continuation of application No. 15/205,613, filed on Jul. 8, 2016.

(60) Provisional application No. 62/191,134, filed on Jul. 10, 2015.

(51) Int. Cl.
*A61N 1/378* (2006.01)
*A61N 1/375* (2006.01)

(58) Field of Classification Search
CPC .......... A61N 1/378; A61N 1/025; A61N 1/08; A61N 1/36153; A61N 1/372; A61N 1/3782; G09G 2330/021; G09G 2300/0426; G09G 2310/0291; G06F 19/3406
See application file for complete search history.

(56) References Cited

U.S. PATENT DOCUMENTS

| | | |
|---|---|---|
| 3,646,940 A | 3/1972 | Timm et al. |
| 3,824,129 A | 7/1974 | Fagan |
| 3,825,015 A | 7/1974 | Berkovits |
| 3,888,260 A | 6/1975 | Fischell |
| 3,902,501 A | 9/1975 | Citron et al. |
| 3,939,843 A | 2/1976 | Smyth |
| 3,942,535 A | 3/1976 | Schulman et al. |
| 3,970,912 A | 7/1976 | Hoffman |
| 3,995,623 A | 12/1976 | Blake et al. |
| 4,019,518 A | 4/1977 | Maurer et al. |
| 4,044,774 A | 8/1977 | Corbin et al. |
| 4,082,097 A | 4/1978 | Mann et al. |
| 4,141,365 A | 2/1979 | Fischell et al. |
| 4,166,469 A | 9/1979 | Littleford |
| 4,269,198 A | 5/1981 | Stokes |
| 4,285,347 A | 8/1981 | Hess |
| 4,340,062 A | 7/1982 | Thompson et al. |
| 4,379,462 A | 4/1983 | Borkan et al. |
| 4,407,303 A | 10/1983 | Akerstroem |
| 4,437,475 A | 3/1984 | White |
| 4,468,723 A | 8/1984 | Hughes |
| 4,512,351 A | 4/1985 | Pohndorf |
| 4,550,731 A | 11/1985 | Batina et al. |
| 4,558,702 A | 12/1985 | Barreras et al. |
| 4,654,880 A | 3/1987 | Sontag |
| 4,662,382 A | 5/1987 | Sluetz et al. |
| 4,673,867 A | 6/1987 | Davis |
| 4,719,919 A | 1/1988 | Marchosky et al. |
| 4,721,118 A | 1/1988 | Harris |
| 4,722,353 A | 2/1988 | Sluetz |
| 4,744,371 A | 5/1988 | Harris |
| 4,800,898 A | 1/1989 | Hess et al. |
| 4,848,352 A | 7/1989 | Pohndorf et al. |
| 4,860,446 A | 8/1989 | Lessar et al. |
| 4,957,118 A | 9/1990 | Erlebacher |
| 4,989,617 A | 2/1991 | Memberg et al. |
| 5,012,176 A | 4/1991 | Laforge |
| 5,052,407 A | 10/1991 | Hauser et al. |
| 5,143,089 A | 9/1992 | Alt |
| 5,193,539 A | 3/1993 | Schulman et al. |
| 5,197,466 A | 3/1993 | Marchosky et al. |
| 5,204,611 A | 4/1993 | Nor et al. |
| 5,255,691 A | 10/1993 | Otten |
| 5,257,634 A | 11/1993 | Kroll |
| 5,342,408 A | 8/1994 | Decoriolis et al. |
| 5,439,485 A | 8/1995 | Mar et al. |
| 5,476,499 A | 12/1995 | Hirschberg |
| 5,484,445 A | 1/1996 | Knuth |
| 5,571,148 A | 11/1996 | Loeb et al. |
| 5,592,070 A | 1/1997 | Mino |
| 5,637,981 A | 6/1997 | Nagai et al. |
| 5,676,162 A | 10/1997 | Larson, Jr. et al. |
| 5,690,693 A | 11/1997 | Wang et al. |
| 5,702,428 A | 12/1997 | Tippey et al. |
| 5,702,431 A | 12/1997 | Wang et al. |
| 5,712,795 A | 1/1998 | Layman et al. |
| 5,713,939 A | 2/1998 | Nedungadi et al. |
| 5,733,313 A | 3/1998 | Barreras, Sr. et al. |
| 5,735,887 A | 4/1998 | Barreras, Sr. et al. |
| 5,741,316 A | 4/1998 | Chen et al. |
| 5,871,532 A | 2/1999 | Schroeppel |
| 5,876,423 A | 3/1999 | Braun |
| 5,877,472 A | 3/1999 | Campbell et al. |
| 5,902,331 A | 5/1999 | Bonner et al. |
| 5,948,006 A | 9/1999 | Mann |
| 5,949,632 A | 9/1999 | Barreras, Sr. et al. |
| 5,957,965 A | 9/1999 | Moumane et al. |
| 5,991,665 A | 11/1999 | Wang et al. |
| 6,027,456 A | 2/2000 | Feler et al. |
| 6,035,237 A | 3/2000 | Schulman et al. |
| 6,052,624 A | 4/2000 | Mann |
| 6,055,456 A | 4/2000 | Gerber |
| 6,057,513 A | 5/2000 | Ushikoshi et al. |
| 6,067,474 A | 5/2000 | Schulman et al. |
| 6,075,339 A | 6/2000 | Reipur et al. |
| 6,076,017 A | 6/2000 | Taylor et al. |
| 6,081,097 A | 6/2000 | Seri et al. |
| 6,083,247 A | 7/2000 | Rutten et al. |
| 6,104,957 A | 8/2000 | Alo et al. |
| 6,104,960 A | 8/2000 | Duysens et al. |
| 6,138,681 A | 10/2000 | Chen et al. |
| 6,164,284 A | 12/2000 | Schulman et al. |
| 6,165,180 A | 12/2000 | Cigaina et al. |
| 6,166,518 A | 12/2000 | Echarri et al. |
| 6,169,387 B1 | 1/2001 | Kaib |
| 6,172,556 B1 | 1/2001 | Prentice |
| 6,178,353 B1 | 1/2001 | Griffith et al. |
| 6,181,105 B1 | 1/2001 | Cutolo et al. |
| 6,185,452 B1 | 2/2001 | Schulman et al. |
| 6,191,365 B1 | 2/2001 | Avellanet |
| 6,208,894 B1 | 3/2001 | Schulman et al. |
| 6,208,895 B1 | 3/2001 | Sullivan et al. |
| 6,212,430 B1 | 4/2001 | Kung |
| 6,212,431 B1 | 4/2001 | Hahn et al. |
| 6,221,513 B1 | 4/2001 | Lasater |
| 6,227,204 B1 | 5/2001 | Baumann et al. |
| 6,243,608 B1 | 6/2001 | Pauly et al. |
| 6,246,911 B1 | 6/2001 | Seligman |
| 6,249,703 B1 | 6/2001 | Stanton et al. |
| 6,265,789 B1 | 7/2001 | Honda et al. |
| 6,275,737 B1 | 8/2001 | Mann |
| 6,278,258 B1 | 8/2001 | Echarri et al. |
| 6,305,381 B1 | 10/2001 | Weijand et al. |
| 6,306,100 B1 | 10/2001 | Prass |
| 6,313,779 B1 | 11/2001 | Leung et al. |
| 6,315,721 B2 | 11/2001 | Schulman et al. |
| 6,316,909 B1 | 11/2001 | Honda et al. |
| 6,321,118 B1 | 11/2001 | Hahn |
| 6,327,504 B1 | 12/2001 | Dolgin et al. |
| 6,354,991 B1 | 3/2002 | Gross et al. |
| 6,360,750 B1 | 3/2002 | Gerber et al. |
| 6,381,496 B1 | 4/2002 | Meadows et al. |
| 6,393,325 B1 | 5/2002 | Mann et al. |
| 6,427,086 B1 | 7/2002 | Fischell et al. |
| 6,438,423 B1 | 8/2002 | Rezai et al. |
| 6,442,434 B1 | 8/2002 | Zarinetchi et al. |
| 6,453,198 B1 | 9/2002 | Torgerson et al. |
| 6,466,817 B1 | 10/2002 | Kaula et al. |
| 6,473,652 B1 | 10/2002 | Sarwal et al. |
| 6,500,141 B1 | 12/2002 | Irion |
| 6,505,075 B1 | 1/2003 | Weiner |
| 6,505,077 B1 | 1/2003 | Kast et al. |
| 6,510,347 B2 | 1/2003 | Borkan |
| 6,516,227 B1 | 2/2003 | Meadow s et al. |
| 6,517,227 B2 | 2/2003 | Stidham et al. |
| 6,521,350 B2 | 2/2003 | Fey et al. |
| 6,542,846 B1 | 4/2003 | Miller et al. |
| 6,553,263 B1 | 4/2003 | Meadows et al. |
| 6,564,807 B1 | 5/2003 | Schulman et al. |
| 6,584,355 B2 | 6/2003 | Stessman |
| 6,600,954 B2 | 7/2003 | Cohen et al. |
| 6,609,031 B1 | 8/2003 | Law et al. |

(56) References Cited

U.S. PATENT DOCUMENTS

| | | |
|---|---|---|
| 6,609,032 B1 | 8/2003 | Woods et al. |
| 6,609,945 B2 | 8/2003 | Jimenez et al. |
| 6,652,449 B1 | 11/2003 | Gross et al. |
| 6,662,051 B1 | 12/2003 | Eraker et al. |
| 6,664,763 B2 | 12/2003 | Echarri et al. |
| 6,685,638 B1 | 2/2004 | Taylor et al. |
| 6,721,603 B2 | 4/2004 | Zabara et al. |
| 6,735,474 B1 | 5/2004 | Loeb et al. |
| 6,745,077 B1 | 6/2004 | Griffith et al. |
| 6,809,701 B2 | 10/2004 | Amundson et al. |
| 6,836,684 B1 | 12/2004 | Rijkhoff et al. |
| 6,847,849 B2 | 1/2005 | Mamo et al. |
| 6,864,755 B2 | 3/2005 | Moore |
| 6,892,098 B2 | 5/2005 | Ayal et al. |
| 6,895,280 B2 | 5/2005 | Meadow s et al. |
| 6,896,651 B2 | 5/2005 | Gross et al. |
| 6,901,287 B2 | 5/2005 | Davis et al. |
| 6,941,171 B2 | 9/2005 | Mann et al. |
| 6,971,393 B1 | 12/2005 | Mamo et al. |
| 6,986,453 B2 | 1/2006 | Jiang et al. |
| 6,989,200 B2 | 1/2006 | Byers et al. |
| 6,990,376 B2 | 1/2006 | Tanagho et al. |
| 6,999,819 B2 | 2/2006 | Sw oyer et al. |
| 7,051,419 B2 | 5/2006 | Schrom et al. |
| 7,054,689 B1 | 5/2006 | Whitehurst et al. |
| 7,069,081 B2 | 6/2006 | Biggs et al. |
| 7,114,502 B2 | 10/2006 | Schulman et al. |
| 7,127,298 B1 | 10/2006 | He et al. |
| 7,131,996 B2 | 11/2006 | Wasserman et al. |
| 7,142,925 B1 | 11/2006 | Bhadra et al. |
| 7,146,219 B2 | 12/2006 | Sieracki et al. |
| 7,151,914 B2 | 12/2006 | Brew er |
| 7,167,749 B2 | 1/2007 | Biggs et al. |
| 7,167,756 B1 | 1/2007 | Torgerson et al. |
| 7,177,690 B2 | 2/2007 | Woods et al. |
| 7,177,698 B2 | 2/2007 | Klosterman et al. |
| 7,181,286 B2 | 2/2007 | Sieracki et al. |
| 7,184,836 B1 | 2/2007 | Meadows et al. |
| 7,187,978 B2 | 3/2007 | Malek et al. |
| 7,191,005 B2 | 3/2007 | Stessman |
| 7,212,110 B1 | 5/2007 | Martin et al. |
| 7,225,028 B2 | 5/2007 | Della Santina et al. |
| 7,225,032 B2 | 5/2007 | Schmeling et al. |
| 7,231,254 B2 | 6/2007 | DiLorenzo |
| 7,234,853 B2 | 6/2007 | Givoletti |
| 7,239,918 B2 | 7/2007 | Strother et al. |
| 7,245,972 B2 | 7/2007 | Davis |
| 7,286,880 B2 | 10/2007 | Olson et al. |
| 7,295,878 B1 | 11/2007 | Meadows et al. |
| 7,305,268 B2 | 12/2007 | Gliner et al. |
| 7,317,948 B1 | 1/2008 | King et al. |
| 7,324,852 B2 | 1/2008 | Barolat et al. |
| 7,324,853 B2 | 1/2008 | Ayal et al. |
| 7,328,068 B2 | 2/2008 | Spinelli et al. |
| 7,330,764 B2 | 2/2008 | Sw oyer et al. |
| 7,331,499 B2 | 2/2008 | Jiang et al. |
| 7,359,751 B1 | 4/2008 | Erickson et al. |
| 7,369,894 B2 | 5/2008 | Gerber |
| 7,386,348 B2 | 6/2008 | North et al. |
| 7,387,603 B2 | 6/2008 | Gross et al. |
| 7,396,265 B2 | 7/2008 | Darley et al. |
| 7,415,308 B2 | 8/2008 | Gerber et al. |
| 7,444,181 B2 | 10/2008 | Shi et al. |
| 7,444,184 B2 | 10/2008 | Boveja et al. |
| 7,450,991 B2 | 11/2008 | Smith et al. |
| 7,460,911 B2 | 12/2008 | Cosendai et al. |
| 7,463,928 B2 | 12/2008 | Lee et al. |
| 7,470,236 B1 | 12/2008 | Kelleher et al. |
| 7,483,752 B2 | 1/2009 | Von Arx et al. |
| 7,486,048 B2 | 2/2009 | Tsukamoto et al. |
| 7,496,404 B2 | 2/2009 | Meadow s et al. |
| 7,513,257 B2 | 4/2009 | Schulman et al. |
| 7,515,967 B2 | 4/2009 | Phillips et al. |
| 7,532,936 B2 | 5/2009 | Erickson et al. |
| 7,539,538 B2 | 5/2009 | Parramon et al. |
| 7,551,960 B2 | 6/2009 | Forsberg et al. |
| 7,555,346 B1 | 6/2009 | Woods et al. |
| 7,565,203 B2 | 7/2009 | Greenberg et al. |
| 7,578,819 B2 | 8/2009 | Bleich et al. |
| 7,580,752 B2 | 8/2009 | Gerber et al. |
| 7,582,053 B2 | 9/2009 | Gross et al. |
| 7,617,002 B2 | 11/2009 | Goetz |
| 7,636,602 B2 | 12/2009 | Baru Fassio et al. |
| 7,640,059 B2 | 12/2009 | Forsberg et al. |
| 7,643,880 B2 | 1/2010 | Tanagho et al. |
| 7,650,192 B2 | 1/2010 | Wahlstrand |
| 7,706,889 B2 | 4/2010 | Gerber et al. |
| 7,720,547 B2 | 5/2010 | Denker et al. |
| 7,725,191 B2 | 5/2010 | Greenberg et al. |
| 7,734,355 B2 | 6/2010 | Cohen et al. |
| 7,738,963 B2 | 6/2010 | Hickman et al. |
| 7,738,965 B2 | 6/2010 | Phillips |
| 7,747,330 B2 | 6/2010 | Nolan et al. |
| 7,771,838 B1 | 8/2010 | He et al. |
| 7,774,069 B2 | 8/2010 | Olson et al. |
| 7,801,619 B2 | 9/2010 | Gerber et al. |
| 7,813,803 B2 | 10/2010 | Heruth et al. |
| 7,813,809 B2 | 10/2010 | Strother et al. |
| 7,826,901 B2 | 11/2010 | Lee et al. |
| 7,848,818 B2 | 12/2010 | Barolat et al. |
| 7,878,207 B2 | 2/2011 | Goetz et al. |
| 7,904,167 B2 | 3/2011 | Klosterman et al. |
| 7,912,555 B2 | 3/2011 | Sw oyer et al. |
| 7,925,357 B2 | 4/2011 | Phillips et al. |
| 7,932,696 B2 | 4/2011 | Peterson |
| 7,933,656 B2 | 4/2011 | Sieracki et al. |
| 7,935,051 B2 | 5/2011 | Miles et al. |
| 7,937,158 B2 | 5/2011 | Erickson et al. |
| 7,952,349 B2 | 5/2011 | Huang et al. |
| 7,957,818 B2 | 6/2011 | Sw oyer |
| 7,979,119 B2 | 7/2011 | Kothandaraman et al. |
| 7,979,126 B2 | 7/2011 | Payne et al. |
| 7,988,507 B2 | 8/2011 | Darley et al. |
| 8,000,782 B2 | 8/2011 | Gharib et al. |
| 8,000,800 B2 | 8/2011 | Takeda et al. |
| 8,000,805 B2 | 8/2011 | Sw oyer et al. |
| 8,005,535 B2 | 8/2011 | Gharib et al. |
| 8,005,549 B2 | 8/2011 | Boser et al. |
| 8,005,550 B2 | 8/2011 | Boser et al. |
| 8,019,423 B2 | 9/2011 | Possover |
| 8,024,047 B2 | 9/2011 | Olson et al. |
| 8,036,756 B2 | 10/2011 | Sw oyer et al. |
| 8,044,635 B2 | 10/2011 | Peterson |
| 8,050,769 B2 | 11/2011 | Gharib et al. |
| 8,055,337 B2 | 11/2011 | Moffitt et al. |
| 8,068,912 B2 | 11/2011 | Kaula et al. |
| 8,083,663 B2 | 12/2011 | Gross et al. |
| 8,103,360 B2 | 1/2012 | Foster |
| 8,116,862 B2 | 2/2012 | Stevenson et al. |
| 8,121,694 B2 | 2/2012 | Molnar et al. |
| 8,121,701 B2 | 2/2012 | Woods et al. |
| 8,129,942 B2 | 3/2012 | Park et al. |
| 8,131,358 B2 | 3/2012 | Moffitt et al. |
| 8,140,168 B2 | 3/2012 | Olson et al. |
| 8,145,324 B1 | 3/2012 | Stevenson et al. |
| 8,150,530 B2 | 4/2012 | Wesselink |
| 8,175,717 B2 | 5/2012 | Haller et al. |
| 8,180,451 B2 | 5/2012 | Hickman et al. |
| 8,180,452 B2 | 5/2012 | Shaquer |
| 8,180,461 B2 | 5/2012 | Mamo et al. |
| 8,214,042 B2 | 7/2012 | Ozaw a et al. |
| 8,214,048 B1 | 7/2012 | Whitehurst et al. |
| 8,214,051 B2 | 7/2012 | Sieracki et al. |
| 8,219,196 B2 | 7/2012 | Torgerson |
| 8,219,202 B2 | 7/2012 | Giftakis et al. |
| 8,224,460 B2 | 7/2012 | Schleicher et al. |
| 8,233,990 B2 | 7/2012 | Goetz |
| 8,255,057 B2 | 8/2012 | Fang et al. |
| 8,311,636 B2 | 11/2012 | Gerber et al. |
| 8,314,594 B2 | 11/2012 | Scott et al. |
| 8,332,040 B1 | 12/2012 | Winstrom |
| 8,340,786 B2 | 12/2012 | Gross et al. |
| 8,362,742 B2 | 1/2013 | Kallmyer |
| 8,369,943 B2 | 2/2013 | Shuros et al. |

(56) References Cited

U.S. PATENT DOCUMENTS

| | | |
|---|---|---|
| 8,386,048 B2 | 2/2013 | McClure et al. |
| 8,417,346 B2 | 4/2013 | Giftakis et al. |
| 8,423,146 B2 | 4/2013 | Giftakis et al. |
| 8,447,402 B1 | 5/2013 | Jiang et al. |
| 8,447,408 B2 | 5/2013 | North et al. |
| 8,457,756 B2 | 6/2013 | Rahman |
| 8,457,758 B2 | 6/2013 | Olson et al. |
| 8,467,875 B2 | 6/2013 | Bennett et al. |
| 8,480,437 B2 | 7/2013 | Dilmaghanian et al. |
| 8,494,625 B2 | 7/2013 | Hargrove |
| 8,515,545 B2 | 8/2013 | Trier |
| 8,538,530 B1 | 9/2013 | Orinski |
| 8,543,223 B2 | 9/2013 | Sage et al. |
| 8,549,015 B2 | 10/2013 | Barolat |
| 8,554,322 B2 | 10/2013 | Olson et al. |
| 8,555,894 B2 | 10/2013 | Schulman et al. |
| 8,562,539 B2 | 10/2013 | Marino |
| 8,571,677 B2 | 10/2013 | Torgerson et al. |
| 8,577,474 B2 | 11/2013 | Rahman et al. |
| 8,588,917 B2 | 11/2013 | Whitehurst et al. |
| 8,588,927 B2 | 11/2013 | Roy et al. |
| 8,612,002 B2 | 12/2013 | Faltys et al. |
| 8,620,436 B2 | 12/2013 | Parramon et al. |
| 8,626,314 B2 | 1/2014 | Sw oyer et al. |
| 8,644,933 B2 | 2/2014 | Ozawa et al. |
| 8,655,451 B2 | 2/2014 | Klosterman et al. |
| 8,700,175 B2 | 4/2014 | Fell |
| 8,706,254 B2 | 4/2014 | Vamos et al. |
| 8,725,262 B2 | 5/2014 | Olson et al. |
| 8,725,269 B2 | 5/2014 | Nolan et al. |
| 8,738,141 B2 | 5/2014 | Smith et al. |
| 8,738,148 B2 | 5/2014 | Olson et al. |
| 8,750,985 B2 | 6/2014 | Parramon et al. |
| 8,761,897 B2 | 6/2014 | Kaula et al. |
| 8,768,452 B2 | 7/2014 | Gerber |
| 8,774,912 B2 | 7/2014 | Gerber |
| 8,855,767 B2 | 10/2014 | Faltys et al. |
| 8,918,174 B2 | 12/2014 | Woods et al. |
| 8,954,148 B2 | 2/2015 | Labbe et al. |
| 8,989,861 B2 | 3/2015 | Su et al. |
| 9,031,658 B2 | 5/2015 | Chiao et al. |
| 9,044,592 B2 | 6/2015 | Imran et al. |
| 9,050,473 B2 | 6/2015 | Woods et al. |
| 9,089,712 B2 | 7/2015 | Joshi et al. |
| 9,108,063 B2 | 8/2015 | Olson et al. |
| 9,144,680 B2 | 9/2015 | Kaula et al. |
| 9,149,635 B2 | 10/2015 | Denison et al. |
| 9,155,885 B2 | 10/2015 | Wei et al. |
| 9,166,321 B2 | 10/2015 | Smith et al. |
| 9,168,374 B2 | 10/2015 | Su |
| 9,192,763 B2 | 11/2015 | Gerber et al. |
| 9,197,173 B2 | 11/2015 | Denison et al. |
| 9,199,075 B1 | 12/2015 | Westlund |
| 9,205,255 B2 | 12/2015 | Strother et al. |
| 9,209,634 B2 | 12/2015 | Cottrill et al. |
| 9,216,294 B2 | 12/2015 | Bennett et al. |
| 9,227,055 B2 | 1/2016 | Wahlstrand et al. |
| 9,227,076 B2 | 1/2016 | Sharma et al. |
| 9,238,135 B2 | 1/2016 | Goetz et al. |
| 9,240,630 B2 | 1/2016 | Joshi |
| 9,242,090 B2 | 1/2016 | Atalar et al. |
| 9,244,898 B2 | 1/2016 | Vamos et al. |
| 9,248,292 B2 | 2/2016 | Trier et al. |
| 9,259,578 B2 | 2/2016 | Torgerson et al. |
| 9,259,582 B2 | 2/2016 | Joshi et al. |
| 9,265,958 B2 | 2/2016 | Joshi et al. |
| 9,270,134 B2 | 2/2016 | Gaddam et al. |
| 9,272,140 B2 | 3/2016 | Gerber et al. |
| 9,283,394 B2 | 3/2016 | Whitehurst et al. |
| 9,295,851 B2 | 3/2016 | Gordon et al. |
| 9,308,022 B2 | 4/2016 | Chitre et al. |
| 9,308,382 B2 | 4/2016 | Strother et al. |
| 9,314,616 B2 | 4/2016 | Wells et al. |
| 9,320,899 B2 | 4/2016 | Parramon et al. |
| 9,333,339 B2 | 5/2016 | Weiner |
| 9,352,148 B2 | 5/2016 | Stevenson et al. |
| 9,352,150 B2 | 5/2016 | Stevenson et al. |
| 9,358,039 B2 | 6/2016 | Kimmel et al. |
| 9,364,658 B2 | 6/2016 | Wechter |
| 9,375,574 B2 | 6/2016 | Kaula et al. |
| 9,393,423 B2 | 7/2016 | Parramon et al. |
| 9,399,137 B2 | 7/2016 | Parker et al. |
| 9,409,020 B2 | 8/2016 | Parker |
| 9,415,211 B2 | 8/2016 | Bradley et al. |
| 9,427,571 B2 | 8/2016 | Sage et al. |
| 9,427,573 B2 | 8/2016 | Gindele et al. |
| 9,433,783 B2 | 9/2016 | Wei et al. |
| 9,436,481 B2 | 9/2016 | Drew |
| 9,446,245 B2 | 9/2016 | Grill et al. |
| 9,463,324 B2 | 10/2016 | Olson et al. |
| 9,468,755 B2 | 10/2016 | Westlund et al. |
| 9,471,753 B2 | 10/2016 | Kaula et al. |
| 9,480,846 B2 | 11/2016 | Strother et al. |
| 9,492,672 B2 | 11/2016 | Vamos et al. |
| 9,492,675 B2 | 11/2016 | Torgerson et al. |
| 9,492,678 B2 | 11/2016 | Chow |
| 9,498,628 B2 | 11/2016 | Kaemmerer et al. |
| 9,502,754 B2 | 11/2016 | Zhao et al. |
| 9,504,830 B2 | 11/2016 | Kaula et al. |
| 9,522,282 B2 | 12/2016 | Chow et al. |
| 9,592,389 B2 | 3/2017 | Moffitt |
| 9,610,449 B2 | 4/2017 | Kaula et al. |
| 9,615,744 B2 | 4/2017 | Denison et al. |
| 9,623,257 B2 | 4/2017 | Olson et al. |
| 9,636,497 B2 | 5/2017 | Bradley et al. |
| 9,643,004 B2 | 5/2017 | Gerber |
| 9,653,935 B2 | 5/2017 | Cong et al. |
| 9,656,074 B2 | 5/2017 | Simon et al. |
| 9,656,076 B2 | 5/2017 | Trier et al. |
| 9,656,089 B2 | 5/2017 | Yip et al. |
| 9,675,809 B2 | 6/2017 | Chow |
| 9,687,649 B2 | 6/2017 | Thacker |
| 9,707,405 B2 | 7/2017 | Shishilla et al. |
| 9,713,706 B2 | 7/2017 | Gerber |
| 9,717,900 B2 | 8/2017 | Swoyer et al. |
| 9,724,526 B2 | 8/2017 | Strother et al. |
| 9,731,116 B2 | 8/2017 | Chen |
| 9,737,704 B2 | 8/2017 | Wahlstrand et al. |
| 9,744,347 B2 | 8/2017 | Chen et al. |
| 9,750,930 B2 | 9/2017 | Chen |
| 9,757,555 B2 | 9/2017 | Novotny et al. |
| 9,764,147 B2 | 9/2017 | Torgerson |
| 9,767,255 B2 | 9/2017 | Kaula et al. |
| 9,776,002 B2 | 10/2017 | Parker et al. |
| 9,776,006 B2 | 10/2017 | Parker et al. |
| 9,776,007 B2 | 10/2017 | Kaula et al. |
| 9,782,596 B2 | 10/2017 | Vamos et al. |
| 9,814,884 B2 | 11/2017 | Parker et al. |
| 9,821,112 B2 | 11/2017 | Olson et al. |
| 9,827,415 B2 | 11/2017 | Stevenson et al. |
| 9,827,424 B2 | 11/2017 | Kaula et al. |
| 9,833,614 B1 | 12/2017 | Gliner |
| 9,849,278 B2 | 12/2017 | Spinelli et al. |
| 9,855,438 B2 | 1/2018 | Parramon et al. |
| 9,872,988 B2 | 1/2018 | Kaula et al. |
| 9,878,165 B2 | 1/2018 | Wilder et al. |
| 9,878,168 B2 | 1/2018 | Shishilla et al. |
| 9,882,420 B2 | 1/2018 | Cong et al. |
| 9,884,198 B2 | 2/2018 | Parker |
| 9,889,292 B2 | 2/2018 | Gindele et al. |
| 9,889,293 B2 | 2/2018 | Siegel et al. |
| 9,889,306 B2 | 2/2018 | Stevenson et al. |
| 9,895,532 B2 | 2/2018 | Kaula et al. |
| 9,899,778 B2 | 2/2018 | Hanson et al. |
| 9,901,284 B2 | 2/2018 | Olsen et al. |
| 9,901,740 B2 | 2/2018 | Drees et al. |
| 9,907,476 B2 | 3/2018 | Bonde et al. |
| 9,907,955 B2 | 3/2018 | Bakker et al. |
| 9,907,957 B2 | 3/2018 | Woods et al. |
| 9,924,904 B2 | 3/2018 | Cong et al. |
| 9,931,513 B2 | 4/2018 | Kelsch et al. |
| 9,931,514 B2 | 4/2018 | Frysz et al. |
| 9,950,171 B2 | 4/2018 | Johanek et al. |
| 9,974,108 B2 | 5/2018 | Polefko |

(56) References Cited

U.S. PATENT DOCUMENTS

| | | |
|---|---|---|
| 9,974,949 B2 | 5/2018 | Thompson et al. |
| 9,981,121 B2 | 5/2018 | Seifert et al. |
| 9,981,137 B2 | 5/2018 | Eiger |
| 9,987,493 B2 | 6/2018 | Torgerson et al. |
| 9,993,650 B2 | 6/2018 | Seitz et al. |
| 9,999,765 B2 | 6/2018 | Stevenson |
| 10,004,910 B2 | 6/2018 | Gadagkar et al. |
| 10,016,596 B2 | 7/2018 | Stevenson et al. |
| 10,027,157 B2 | 7/2018 | Labbe et al. |
| 10,045,764 B2 | 8/2018 | Scott et al. |
| 10,046,164 B2 | 8/2018 | Gerber |
| 10,047,782 B2 | 8/2018 | Sage et al. |
| 10,052,490 B2 | 8/2018 | Kaula et al. |
| 10,065,044 B2 | 9/2018 | Sharma et al. |
| 10,071,247 B2 | 9/2018 | Childs |
| 10,076,661 B2 | 9/2018 | Wei et al. |
| 10,076,667 B2 | 9/2018 | Kaula et al. |
| 10,083,261 B2 | 9/2018 | Kaula et al. |
| 10,086,191 B2 | 10/2018 | Bonde et al. |
| 10,086,203 B2 | 10/2018 | Kaemmerer |
| 10,092,747 B2 | 10/2018 | Sharma et al. |
| 10,092,749 B2 | 10/2018 | Stevenson et al. |
| 10,095,837 B2 | 10/2018 | Corey et al. |
| 10,099,051 B2 | 10/2018 | Stevenson et al. |
| 10,103,559 B2 | 10/2018 | Cottrill et al. |
| 10,109,844 B2 | 10/2018 | Dai et al. |
| 10,118,037 B2 | 11/2018 | Kaula et al. |
| 10,124,164 B2 | 11/2018 | Stevenson et al. |
| 10,124,171 B2 | 11/2018 | Kaula et al. |
| 10,124,179 B2 | 11/2018 | Norton et al. |
| 10,141,545 B2 | 11/2018 | Kraft et al. |
| 10,173,062 B2 | 1/2019 | Parker |
| 10,179,241 B2 | 1/2019 | Walker et al. |
| 10,179,244 B2 | 1/2019 | Lebaron et al. |
| 10,183,162 B2 | 1/2019 | Johnson et al. |
| 10,188,857 B2 | 1/2019 | North et al. |
| 10,195,419 B2 | 2/2019 | Shiroff et al. |
| 10,206,710 B2 | 2/2019 | Kern et al. |
| 10,213,229 B2 | 2/2019 | Chitre et al. |
| 10,220,210 B2 | 3/2019 | Walker et al. |
| 10,226,617 B2 | 3/2019 | Finley et al. |
| 10,226,636 B2 | 3/2019 | Gaddam et al. |
| 10,236,709 B2 | 3/2019 | Decker et al. |
| 10,238,863 B2 | 3/2019 | Gross et al. |
| 10,238,877 B2 | 3/2019 | Kaula et al. |
| 10,244,956 B2 | 4/2019 | Kane |
| 10,245,434 B2 | 4/2019 | Kaula et al. |
| 10,258,800 B2 | 4/2019 | Perryman et al. |
| 10,265,532 B2 | 4/2019 | Carcieri et al. |
| 10,277,055 B2 | 4/2019 | Peterson et al. |
| 10,293,168 B2 | 5/2019 | Bennett et al. |
| 10,328,253 B2 | 6/2019 | Wells |
| 10,363,419 B2 | 7/2019 | Simon et al. |
| 10,369,275 B2 | 8/2019 | Olson et al. |
| 10,369,370 B2 | 8/2019 | Shishilla et al. |
| 10,376,701 B2 | 8/2019 | Kaula et al. |
| 10,448,889 B2 | 10/2019 | Gerber et al. |
| 10,456,574 B2 | 10/2019 | Chen et al. |
| 10,471,262 B2 | 11/2019 | Perryman et al. |
| 10,485,970 B2 | 11/2019 | Gerber et al. |
| 10,493,282 B2 | 12/2019 | Caparso et al. |
| 10,493,287 B2 | 12/2019 | Yoder et al. |
| 10,561,835 B2 | 2/2020 | Gerber |
| 2002/0040185 A1 | 4/2002 | Atalar et al. |
| 2002/0051550 A1 | 5/2002 | Leysieffer |
| 2002/0051551 A1 | 5/2002 | Leysieffer et al. |
| 2002/0116042 A1 | 8/2002 | Boling |
| 2002/0140399 A1 | 10/2002 | Echarri et al. |
| 2002/0156513 A1 | 10/2002 | Borkan |
| 2002/0177884 A1 | 11/2002 | Ahn et al. |
| 2003/0028072 A1 | 2/2003 | Fischell et al. |
| 2003/0078633 A1 | 4/2003 | Firlik et al. |
| 2003/0114899 A1 | 6/2003 | Woods et al. |
| 2003/0212440 A1 | 11/2003 | Boveja |
| 2004/0098068 A1 | 5/2004 | Carbunaru et al. |
| 2004/0106963 A1 | 6/2004 | Tsukamoto et al. |
| 2004/0210290 A1 | 10/2004 | Omar-Pasha |
| 2004/0250820 A1 | 12/2004 | Forsell |
| 2004/0267137 A1 | 12/2004 | Peszynski et al. |
| 2005/0004619 A1 | 1/2005 | Wahlstrand et al. |
| 2005/0004621 A1 | 1/2005 | Boveja et al. |
| 2005/0021108 A1 | 1/2005 | Klosterman et al. |
| 2005/0075693 A1 | 4/2005 | Toy et al. |
| 2005/0075694 A1 | 4/2005 | Schmeling et al. |
| 2005/0075696 A1 | 4/2005 | Forsberg et al. |
| 2005/0075697 A1 | 4/2005 | Olson et al. |
| 2005/0075698 A1 | 4/2005 | Phillips et al. |
| 2005/0075699 A1 | 4/2005 | Olson et al. |
| 2005/0075700 A1 | 4/2005 | Schommer et al. |
| 2005/0104577 A1 | 5/2005 | Matei et al. |
| 2005/0187590 A1 | 8/2005 | Boveja et al. |
| 2005/0267546 A1 | 12/2005 | Parramon et al. |
| 2006/0016452 A1 | 1/2006 | Goetz et al. |
| 2006/0050539 A1 | 3/2006 | Yang et al. |
| 2006/0142822 A1 | 6/2006 | Tulgar |
| 2006/0149345 A1 | 7/2006 | Boggs et al. |
| 2006/0200205 A1 | 9/2006 | Haller |
| 2006/0206166 A1 | 9/2006 | Weiner |
| 2007/0032836 A1 | 2/2007 | Thrope et al. |
| 2007/0073357 A1 | 3/2007 | Rooney et al. |
| 2007/0239224 A1 | 10/2007 | Bennett et al. |
| 2007/0265675 A1 | 11/2007 | Lund et al. |
| 2007/0293914 A1 | 12/2007 | Woods et al. |
| 2008/0065182 A1 | 3/2008 | Pack et al. |
| 2008/0132961 A1 | 6/2008 | Jaax et al. |
| 2008/0132969 A1 | 6/2008 | Bennett et al. |
| 2008/0154335 A1 | 6/2008 | Mrva et al. |
| 2008/0161874 A1 | 7/2008 | Bennett et al. |
| 2008/0172109 A1 | 7/2008 | Rahman et al. |
| 2008/0183236 A1 | 7/2008 | Gerber |
| 2008/0278974 A1 | 11/2008 | Wu |
| 2009/0088816 A1 | 4/2009 | Harel et al. |
| 2009/0105785 A1 | 4/2009 | Wei et al. |
| 2009/0112291 A1 | 4/2009 | Wahlstrand et al. |
| 2009/0259273 A1 | 10/2009 | Figueiredo et al. |
| 2010/0076254 A1 | 3/2010 | Jimenez et al. |
| 2010/0076534 A1 | 3/2010 | Mock |
| 2010/0100158 A1 | 4/2010 | Thrope et al. |
| 2011/0137378 A1 | 6/2011 | Klosterman et al. |
| 2011/0152959 A1 | 6/2011 | Sherwood et al. |
| 2011/0257701 A1 | 10/2011 | Strother et al. |
| 2011/0278948 A1 | 11/2011 | Forsell |
| 2011/0282416 A1 | 11/2011 | Hamann et al. |
| 2011/0301667 A1 | 12/2011 | Olson et al. |
| 2012/0016447 A1 | 1/2012 | Zhu et al. |
| 2012/0041512 A1 | 2/2012 | Weiner |
| 2012/0046712 A1 | 2/2012 | Woods et al. |
| 2012/0071950 A1 | 3/2012 | Archer |
| 2012/0095529 A1 | 4/2012 | Parramon et al. |
| 2012/0109258 A1 | 5/2012 | Cinbis et al. |
| 2012/0119698 A1 | 5/2012 | Karalis et al. |
| 2012/0130448 A1 | 5/2012 | Woods et al. |
| 2012/0259381 A1 | 10/2012 | Smith et al. |
| 2012/0262108 A1 | 10/2012 | Olson et al. |
| 2012/0274270 A1 | 11/2012 | Dinsmoor et al. |
| 2012/0276854 A1 | 11/2012 | Joshi et al. |
| 2012/0276856 A1 | 11/2012 | Joshi et al. |
| 2013/0004925 A1 | 1/2013 | Labbe et al. |
| 2013/0006330 A1 | 1/2013 | Wilder et al. |
| 2013/0006331 A1 | 1/2013 | Weisgarber et al. |
| 2013/0023958 A1 | 1/2013 | Fell |
| 2013/0096651 A1 | 4/2013 | Ozawa |
| 2013/0148768 A1 | 6/2013 | Kim |
| 2013/0150925 A1 | 6/2013 | Vamos et al. |
| 2013/0197608 A1 | 8/2013 | Eiger |
| 2013/0207863 A1 | 8/2013 | Joshi |
| 2013/0211479 A1 | 8/2013 | Olson et al. |
| 2013/0289665 A1 | 10/2013 | Marnfeldt et al. |
| 2013/0303942 A1 | 11/2013 | Damaser et al. |
| 2013/0310894 A1 | 11/2013 | Trier |
| 2013/0331909 A1 | 12/2013 | Gerber |
| 2014/0180361 A1 | 6/2014 | Burdick et al. |
| 2014/0222112 A1 | 8/2014 | Fell |
| 2014/0237806 A1 | 8/2014 | Smith et al. |

(56) References Cited

U.S. PATENT DOCUMENTS

| | | |
|---|---|---|
| 2014/0257121 A1 | 9/2014 | Feldman et al. |
| 2014/0277268 A1 | 9/2014 | Lee |
| 2014/0277270 A1 | 9/2014 | Parramon et al. |
| 2015/0066108 A1 | 3/2015 | Shi et al. |
| 2015/0088227 A1 | 3/2015 | Shishilla et al. |
| 2015/0123608 A1 | 5/2015 | Dearden et al. |
| 2015/0214604 A1 | 7/2015 | Zhao et al. |
| 2017/0007836 A1 | 1/2017 | Nassif |
| 2017/0197079 A1 | 7/2017 | Illegems et al. |
| 2017/0340878 A1 | 11/2017 | Wahlstrand et al. |
| 2018/0021587 A1 | 1/2018 | Strother et al. |
| 2018/0036477 A1 | 2/2018 | Olson et al. |
| 2019/0269918 A1 | 9/2019 | Parker |
| 2019/0351244 A1 | 11/2019 | Shishilla et al. |
| 2019/0358395 A1 | 11/2019 | Olson et al. |

FOREIGN PATENT DOCUMENTS

| | | |
|---|---|---|
| AU | 5123800 | 11/2000 |
| CA | 2371378 | 11/2000 |
| CA | 2554676 | 9/2005 |
| CN | 101495174 A | 7/2009 |
| CN | 102202729 A | 9/2011 |
| CN | 103079633 A | 5/2013 |
| DE | 3146182 | 6/1983 |
| DE | 102010006837 A1 | 8/2011 |
| EP | 0656218 | 6/1995 |
| EP | 1205004 | 5/2002 |
| EP | 1680182 A1 | 7/2006 |
| EP | 1904153 B1 | 4/2008 |
| EP | 2243509 A1 | 10/2010 |
| ES | 2395128 | 2/2013 |
| HK | 1098715 | 3/2012 |
| JP | 2003047179 A | 2/2003 |
| JP | 2007268293 | 10/2007 |
| JP | 4125357 | 7/2008 |
| JP | 2014514043 | 6/2014 |
| WO | 9820933 | 5/1998 |
| WO | 9918879 | 4/1999 |
| WO | 9934870 | 7/1999 |
| WO | 9942173 | 8/1999 |
| WO | WO 88/56677 A1 | 3/2000 |
| WO | 0065682 | 11/2000 |
| WO | 0069012 | 11/2000 |
| WO | WO 2000-066221 A1 | 11/2000 |
| WO | 0183029 | 11/2001 |
| WO | WO 2002-003408 A2 | 1/2002 |
| WO | WO 2002-009808 A1 | 2/2002 |
| WO | 2004021876 | 3/2004 |
| WO | WO 2004-103465 A1 | 12/2004 |
| WO | 2005079295 | 9/2005 |
| WO | 2005081740 | 9/2005 |
| WO | WO 2008/021524 A2 | 2/2008 |
| WO | 2008/049199 A1 | 5/2008 |
| WO | WO 2009-051539 A1 | 4/2009 |
| WO | WO 2009-091267 A2 | 7/2009 |
| WO | WO 2010-042056 A1 | 4/2010 |
| WO | WO 2010-042057 A1 | 4/2010 |
| WO | WO 2011/059565 A1 | 5/2011 |
| WO | WO 2013-141844 | 9/2013 |

OTHER PUBLICATIONS

Boiocchi, S., et al., "Self-calibration in high speed current steering CMOS D/A converters", Advanced A-D and D-A Conversion Techniques and Their Applications, 1994, Second International Conference on Cambridge, UK, London, UK, IEEE, UK, Jan. 1, 1994 (Jan. 1, 1994), pp. 148-152.

Bosch, J., et al., Sacral (S3) Segmental Nerve Stimulation as a Treatment for Urge Incontinence in Patients With Detrusor Instability: Results of Chronic Electrical Stimulation Using an Implantable Neural Prosthesis, The Journal of Urology, Aug. 1995, vol. 154, pp. 504-507.

Ghovanloo, M., et al., A Small Size Large Voltage Compliance Programmable Current Source for Biomedical Implantable Microstimulators, Proceedings of the 25th Annual International Conference of the IEEE EMBS, Sep. 17-21, 2003, pp. 1979-1982.

Gudnason, G., "A low-power ASK demodulator for Inductively coupled implantable electronics", Solid-State Circuits Conference, 2000, Esscirc "00, Proceedings of the 26rd European, IEEE, Sep. 19, 2000, pp. 385-388.

Humayun, M.S., et al., "A Variable Range Bi-Phasic Current Stimulus Driver Circuitry for an Implantable Retinal Prosthetic Device", IEEE Journal of Solid-State Circuits, IEEE Service Center, Piscataway, NJ, USA, vol. 40, No. 3, Mar. 1, 2005, (Mar. 1, 2005), pp. 763-771.

Liu, W., et al., "A Neuro-Stimulus Chip with Telemetry Unit for Retinal Prosthetic Device", IEEE Journal of Solid-State Circuits, vol. 35, No. 10, Oct. 2000, pp. 1487-1497.

Tanagho, E., et al., Bladder Pacemaker: Scientific Basis and Clinical Future, Urology, Dec. 1982, vol. 20, No. 6, pp. 614-619.

Nag, S., et al., "Flexible Charge Balanced Stimulator With 5.6 fC Accuracy for 140 nC Injections", IEE Transactions on Biomedical Circuits and Systems, vol. 7, No. 3, 3, Jun. 2013, pp. 266-275.

Van Paemel, M., "High-Efficiency Transmission for Medical Implants", IEEE Solid-State Circuits Magazine, IEEE, USA, vol. 3, No. 1, Jan. 1, 2011, pp. 47-59.

Wang, Chua-Chin, et al., "A 140-dB CMRR Low-noise Instrumentation Amplifier for Neural Signal Sensing", Circutis and Systems, 2006, APCCAS 2006, IEEE Asia Pacific Conference on IEEE, Piscataway, NJ, USA, Dec. 1, 2006 (Dec. 1, 2006), pp. 696-699.

Von Arx, J.A., et al., "A Wireless Single-Chip Telemetry-Powered Neural Stimulation System", IEEE International Solid-State Circuits Conference, ISSCC99, Session 12, Paper TP 12.6, Feb. 16, 1999, pp. 215-216.

U.S. Appl. No. 62/191,134, filed Jul. 10, 2015.
U.S. Appl. No. 62/038,122, filed Aug. 15, 2014.
U.S. Appl. No. 62/038,131, filed Aug. 15, 2014.
U.S. Appl. No. 62/041,611, filed Aug. 25, 2014.
U.S. Appl. No. 62/110,274, filed Jan. 30, 2015.
U.S. Appl. No. 62/101,888, filed Jan. 9, 2015.
U.S. Appl. No. 62/101,899, filed Jan. 9, 2015.
U.S. Appl. No. 62/101,897, filed Jan. 9, 2015.
U.S. Appl. No. 62/101,666, filed Jan. 9, 2015.
U.S. Appl. No. 62/101,884, filed Jan. 9, 2015.
U.S. Appl. No. 62/101,782, filed Jan. 9, 2015.

Paralikar., et al., A Fully Implantable and Rechargeable Neurostimulation System for Animal Research, 7th Annual International IEEE EMBS Conference of Neural Engineering, Montpellier, France, Apr. 22-24, 2015, pp. 418-421.

"Bu-802a: How does Rising Internal Resistance Affect Performance? Understanding the", BatteryUniversity.com, Available Online at https://batteryuniversity.com/learn/article/rising_internal_resistance, Accessed from Internet on: May 15, 2020, 10 pages.

"Changing Standards for Medical Equipment", UL 544 and UL 187 vs. UL 2601 ("Smith"), 8 pages.

"DOE Handbook: Primer on Lead-Acid Storage Batteries", U.S. Dept. of Energy, Available Online at htt12s://www.stan dards.doe.gov/standards- documents/ I 000/1084-bhdbk-1995/©©images/file, Sep. 1995, 54 pages.

"Medical Electrical Equipment—Part 1: General Requirements for Safety", British Standard, BS EN 60601-1:1990-BS5724-1:1989, Mar. 1979, 200 pages.

"Summary of Safety and Effectiveness", Medtronic InterStim System for Urinary Control, Apr. 15, 1999, pp. 1-18.

"The Advanced Bionics PRECISION™ Spinal Cord Stimulator System", Advanced Bionics Corporation, Apr. 27, 2004, pp. 1-18.

"UL Standard for Safety for Medical and Dental Equipment", UL 544, 4th edition, Dec. 30, 1998, 128 pages.

Barnhart et al., "A Fixed-Rate Rechargeable Cardiac Pacemaker", APL Technical Digest, Jan.-Feb. 1970, pp. 2-9.

Benditt et al., "A Combined Atrial/Ventricular Lead for Permanent Dual-Chamber Cardiac Pacing Applications", Chest, vol. 83, pp. 929-931, 1983.

(56) References Cited

OTHER PUBLICATIONS

Boyce et al., "Research Related to the Development of an Artificial Electrical Stimulator for the Paralyzed Human Bladder: a Review", The Journal of Urology, vol. 91, No. 1, Jan. 1964, pp. 41-51.

Bradley et al., "Further Experience With the Radio Transmitter Receiver Unit for the Neurogenic Bladder", Journal of Neurosurgery, vol. 20, No. 11, Nov. 1963, pp. 953-960.

Broggi et al., "Electrical Stimulation of the Gasserian Ganglion for Facial Pain: Preliminary Results", Acta Neurochirurgica, vol. 39, 1987, pp. 144-146.

Cameron et al., "Effects of Posture on Stimulation Parameters in Spinal Cord Stimulation", Neuromodulation, vol. 1, No. 4, 1998, pp. 177-183.

Connelly et al., "Atrial Pacing Leads Following Open Heart Surgery: Active or Passive Fixation?", Pacing and Clinical Electrophysiology, vol. 20, No. 10, Oct. 1997, pp. 2429-2433.

Fischell, "The Development of Implantable Medical Devices at the Applied Physics Laboratory", Johns Hopkins APL Technical Digest, vol. 13 No. 1, 1992, pp. 233-243.

Gaunt et al., "Control of Urinary Bladder Function With Devices: Successes and Failures", Progress in Brain Research, vol. 152, 2006, pp. 1-24.

Helland, "Technical Improvements to be Achieved by the Year 2000: Leads and Connector Technology", Rate Adaptive Cardiac Pacing, Springer Verlag, 1993, pp. 279-292.

Hidefjall "The Pace of Innovation—Patterns of Innovation in the Cardiac Pacemaker Industry", Linkoping University Press, 1997, 398 pages.

Ishihara et al., "A Comparative Study of Endocardial Pacemaker Leads", Cardiovascular Surgery, Nagoya Ekisaikai Hospital, 1st Dept. of Surgery, Nagoya University School of Medicine, 1981, pp. 132-135.

Jonas et al., "Studies on the Feasibility of Urinary Bladder Evacuation by Direct Spinal Cord Stimulation. I. Parameters of Most Effective Stimulation", Investigative urology, vol. 13, No. 2, 1975, pp. 142-150.

Kakuta et al., "In Vivo Long Term Evaluation of Transcutaneous Energy Transmission for Totally Implantable Artificial Heart", ASAIO Journal, Mar.-Apr. 2000, pp. 1-2.

Kester et al., "Voltage-to-Frequency Converters", Available Online at https://www.analog.com/media/cn/training-seminars/tutorials/MT-028.pdf, 7 pages.

Lazorthes et al., "Chronic Stimulation of the Gasserian Ganglion for Treatment of Atypical Facial Neuralgia", Pacing and Clinical Electrophysiology, vol. 10, Jan.-Feb. 1987, pp. 257-265.

Lewis et al., "Early Clinical Experience with the Rechargeable Cardiac Pacemaker", The Annals of Thoracic Surgery, vol. 18, No. 5, Nov. 1974, pp. 490-493.

Love et al., "Experimental Testing of a Permanent Rechargeable Cardiac Pacemaker", The Annals of Thoracic Surgery, vol. 17, No. 2, Feb. 1, 1974, pp. 152-156.

Love, "Pacemaker Troubleshooting and Follow-up", Clinical Cardiac Pacing, Defibrillation, and Resynchronization Therapy, Chapter 24, 2007, pp. 1005-1062.

Madigan et al., "Difficulty of Extraction of Chronically Implanted Tined Ventricular Endocardial Leads", Journal of the American College of Cardiology, vol. 3, No. 3, Mar. 1984, pp. 724-731.

Meglio, "Percutaneously Implantable Chronic Electrode for Radiofrequency Stimulation of the Gasserian Ganglion. A Perspective in the Management of Trigeminal Pain", Acta Neurochirurgica, vol. 33, 1984, pp. 521-525.

Meyerson, "Alleviation of Atypical Trigeminal Pain by Stimulation of the Gasserian Ganglion via an Implanted Electrode", Acta Neurochirurgica Supplementum, vol. 30, 1980, pp. 303-309.

Mitamura et al., "Development of Transcutaneous Energy Transmission System", Available Online at https://www.researchgate.net/publication/312810915 Ch.28, Jan. 1988, pp. 265-270.

Nakamura et al., "Biocompatibility and Practicality Evaluations of Transcutaneous Energy Transmission Unit for the Totally Implantable Artifical Heart System", Journal of Artificial Organs, vol. 27, No. 2, 1998, pp. 347-351.

Nashold et al., "Electromicturition in Paraplegia. Implantation of a Spinal Neuroprosthesis", Arch Surg., vol. 104, Feb. 1972, pp. 195-202.

Painter et al., "Implantation of an Endocardial Tined Lead to Prevent Early Dislodgement", The Journal of Thoracic and Cardiovascular Surgery, vol. 77, No. 2, Feb. 1979, pp. 249-251.

Perez, "Lead-Acid Battery State of Charge vs. Voltage", Available Online at http://www.rencobattery.com/resources/SOC vs-Voltage.pdf, Aug.-Sep. 1993, 5 pages.

Schaldach et al., "A Long-Lived, Reliable, Rechargeable Cardiac Pacemaker", Engineering in Medicine, vol. 1: Advances in Pacemaker Technology, 1975, 34 pages.

Scheuer-Leeser et al., "Polyurethane Leads: Facts and Controversy", PACE, vol. 6, Mar.-Apr. 1983, pp. 454-458.

Tanagho, "Neuromodulation and Neurostimulation: Overview and Future Potential", Translational Androl Urol, vol. 1, No. 1, 2012, pp. 44-49.

Torres et al., "Electrostatic Energy-Harvesting and Battery-Charging CMOS System Prototype", Available Online at http://rincon-mora.gatech.edu/12ublicat/jmls/tcasi09_hrv_sys.pdf, pp. 1-10.

Young, "Electrical Stimulation of the Trigeminal Nerve Root for the Treatment of Chronic Facial Pain", Journal of Neurosurgery, vol. 83, No. 1, Jul. 1995, pp. 72-78.

IMPLANTABLE NERVE STIMULATOR HAVING INTERNAL ELECTRONICS WITHOUT ASIC AND METHODS OF USE

CROSS-REFERENCES TO RELATED APPLICATIONS

This application is divisional of U.S. application Ser. No. 15/414,531, filed Jan. 24, 2017, and entitled "IMPLANTABLE NERVE STIMULATOR HAVING INTERNAL ELECTRONICS WITHOUT ASIC AND METHODS OF USE", which is a continuation of U.S. application Ser. No. 15/205,613, filed on Jul. 8, 2016, and entitled "IMPLANTABLE NERVE STIMULATOR HAVING INTERNAL ELECTRONICS WITHOUT ASIC AND METHODS OF USE"; which claims the benefit of U.S. Provisional Application No. 62/191,134, filed Jul. 10, 2015, and entitled "IMPLANTABLE NERVE STIMULATOR HAVING INTERNAL ELECTRONICS WITHOUT ASIC AND METHODS OF USE," the entirety of each which is hereby incorporated by reference herein. The present application is related to U.S. Provisional Patent Application Nos. 62/038,122 filed on Aug. 15, 2014 and entitled "Devices and Methods for Anchoring of Neurostimulation Leads"; 62/038,131, filed on Aug. 15, 2014 and entitled "External Pulse Generator Device and Associated Methods for Trial Nerve Stimulation"; 62/041,611, filed on Aug. 25, 2014 and entitled "Electromyographic Lead Positioning and Stimulation Titration in a Nerve Stimulation System for Treatment of Overactive Bladder, Pain and Other Indicators"; 62/110,274, filed on Jan. 30, 2015 and entitled "Implantable Lead Affixation Structure for Nerve Stimulation to Alleviate Bladder Dysfunction and Other Indications"; and U.S. Provisional Patent Application Nos. 62/101,888, entitled "Electromyographic Lead Positioning and Stimulation Titration in a Nerve Stimulation System for Treatment of Overactive Bladder" 62/101,899, entitled "Integrated Electromyographic Clinician Programmer For Use With an Implantable Neurostimulator;" 62/101,897, entitled "Systems and Methods for Neurostimulation Electrode Configurations Based on Neural Localization;" 62/101,666, entitled "Patient Remote and Associated Methods of Use With a Nerve Stimulation System;" 62/101,884, entitled "Attachment Devices and Associated Methods of Use With a Nerve Stimulation Charging Device; 62/101,782, entitled "Improved Antenna and Methods of Use For an Implantable Nerve Stimulator," all filed on Jan. 9, 2015; each of which is assigned to the same assignee and incorporated herein by reference in its entirety for all purposes.

BACKGROUND

The present disclosure relates to neurostimulation treatment systems and associated devices, as well as methods of treatment, implantation and configuration of such treatment systems.

Treatments with implantable neurostimulation systems have become increasingly common in recent years. While such systems have shown promise in treating a number of conditions, effectiveness of treatment may vary considerably between patients. A number of factors may lead to the very different outcomes that patients experience and viability of treatment can be difficult to determine before implantation. For example, stimulation systems often make use of an array of electrodes to treat one or more target nerve structures. The electrodes are often mounted together on a multi-electrode lead, and the lead implanted in tissue of the patient at a position that is intended to result in electrical coupling of the electrode to the target nerve structure, typically with at least a portion of the coupling being provided via intermediate tissues. Other approaches may also be employed, for example, with one or more electrodes attached to the skin overlying the target nerve structures, implanted in cuffs around a target nerve, or the like. Regardless, the physician will typically seek to establish an appropriate treatment protocol by varying the electrical stimulation that is applied to the electrodes.

Current stimulation electrode placement/implantation techniques and known treatment setting techniques suffer from significant disadvantages. The nerve tissue structures of different patients can be quite different, with the locations and branching of nerves that perform specific functions and/or enervate specific organs being challenging to accurately predict or identify. The electrical properties of the tissue structures surrounding a target nerve structure may also be quite different among different patients, and the neural response to stimulation may be markedly dissimilar, with an electrical stimulation pulse pattern, frequency, and/or voltage that is effective to affect a body function for one patient may impose significant pain on, or have limited effect for, another patient. Even in patients where implantation of a neurostimulation system provides effective treatment, frequent adjustments and changes to the stimulation protocol are often required before a suitable treatment program can be determined, often involving repeated office visits and significant discomfort for the patient before efficacy is achieved. While a number of complex and sophisticated lead structures and stimulation setting protocols have been implemented to seek to overcome these challenges, the variability in lead placement results, the clinician time to establish suitable stimulation signals, and the discomfort (and in cases of significant pain) that is imposed on the patient remain less than ideal. In addition, the lifetime and battery life of such devices is relatively short, such that implanted systems are routinely replaced every few years, which requires additional surgeries, patient discomfort, and significant costs to healthcare systems.

Furthermore, current stimulation systems rely on elaborate circuit designs to manage the sourcing and sinking of current to the electrodes. In many instances, the complexity of theses circuits is such that they are placed in an application-specific integrated circuit (ASIC). Such an ASIC provides benefits in that an ASIC allows compact packaging of circuits which compact packaging is beneficial in the field of implantable devices. However, ASICs are expensive to design and manufacture and have lengthy turn-around times when a new ASIC design is desired.

The tremendous benefits of these neural stimulation therapies have not yet been fully realized. Therefore, it is desirable to provide improved neurostimulation methods, systems and devices, as well as methods for implanting and configuring such neurostimulation systems for a particular patient or condition being treated. It would be particularly helpful to provide such systems and methods so as to improve ease of use by the physician in implanting and configuring the system, as well as to improve patient comfort and alleviation of symptoms for the patient, and/or to provide a redesigned circuit for current sourcing and sinking to improve the manufacturability and controllability of the implantable device.

BRIEF SUMMARY

The present disclosure relates to implantable neurostimulators, and, more specifically, to an implantable pulse generator (IPG). The IPG can include current source/sinks that are configured to selectably source current to, and sink current from, target tissue. This ability of the current source/sinks to selectably source current to and sink current from target tissue decreases the number of components within the IPG and thus enables smaller and more compact IPGs. Additionally, such selectable current source/sinks provide the benefit of being able to be made with off-the-shelf components while still maintaining a small size. Accordingly, IPGs with such current source/sinks can eliminate an ASIC that had been used for current sourcing/sinking. The elimination of this ASIC decreases the design and manufacturing costs of the IPG, and enables quicker and easier design changes.

The current source/sinks can be configured to selectably source current to and sink current from target tissue via a current drive differential amplifier. The current driver differential amplifier selectively sources or sinks current based on the voltage supplied to its inverting and non-inverting inputs. In some embodiments, the inverting input of the current driver differential amplifier can be supplied with a voltage that is intermediate between a maximum and minimum voltage supplyable to the non-inverting input of the current drive differential amplifier. In such an embodiment, the voltage provided to the non-inverting input of the current drive differential amplifier can be selected to cause the current drive differential amplifier to either source current to, or sink current from, the target tissue.

One aspect of the present disclosure relates to an implantable neurostimulator system for delivering one or more electrical pulses to a target region within a patient's body. The implantable neurostimulator system includes an implantable lead having a plurality of electrodes located on a distal end of the lead, which electrodes are positionable proximate to a target region within a patient's body to provide electrical stimulation to the target region, and an implantable pulse generator electrically coupled to a proximal end of the lead. In some embodiments, the implantable pulse generator includes: a bio-compatible housing defining a hermetically sealed internal volume; a rechargeable power supply disposed within the hermetically sealed internal volume of the bio-compatible housing; and circuitry disposed within the hermetically sealed internal volume of the bio-compatible housing. In some embodiments, this circuitry is electrically coupled to the rechargeable power supply and configured to generate one or more electrical pulses. In some embodiments, the circuitry includes a first differential amplifier that can selectively source current to the lead and can selectively sink current from the lead.

In some embodiments, the circuitry further includes a second differential amplifier that can selectively source current to the lead and selectively sink current from the lead. In some embodiments, the second differential amplifier can be selected to sink current from at least one of the plurality of electrodes located on the lead when the first differential amplifier is selected to source current to at least another one of the plurality of electrodes located on the lead. In some embodiments, the second differential amplifier can be selected to source current to the at least one of the plurality of electrodes located on the lead when the first differential amplifier is selected to sink current from the at least another one of the plurality of electrodes located on the lead.

In some embodiments, the first differential amplifier includes a non-inverting input coupled to a current command configured to supply a voltage within a first range to the non-inverting input, and in some embodiments, the first differential amplifier includes an inverting input coupled to a virtual ground. In some embodiments, the first range of supplied voltage has a maximum voltage and a minimum voltage, and the difference in voltage between the maximum voltage and the minimum voltage of the first range is at least 5 volts. In some embodiments, the virtual ground has a ground voltage between the maximum voltage and the minimum voltage of the supplied voltage.

In some embodiments, the virtual ground coupled to the inverting input of the first differential amplifier has a voltage at the inverting input that is equal to the ground voltage of the virtual ground when the circuitry is operating at a steady state. In some embodiments, the first differential amplifier can source current when the supplied voltage applied to the non-inverting input of the first differential amplifier is greater than the ground voltage of the virtual ground. In some embodiments, the first differential amplifier can sink current when the supplied voltage applied to the non-inverting input of the first differential amplifier is less than the ground voltage of the virtual ground.

One aspect of the present disclosure relates to an implantable neurostimulator for delivering one or more electrical pulses to a target region within a patient's body with an implantable lead comprising a plurality of electrodes positionable proximate to the target region and electrically coupleable thereto. The implantable neurostimulator includes a bio-compatible housing defining a hermetically sealed internal volume that can be implanted within a body of a patient, a rechargeable battery disposed within the hermetically sealed internal volume of the bio-compatible housing and circuitry disposed within the hermetically sealed internal volume of the bio-compatible housing. This circuitry can be electrically coupled to the rechargeable power supply and can generate one or more electrical pulses. The circuitry includes a first current control module and a second current control module. In some embodiments, each of the first and the second current control modules include a current drive differential amplifier having a non-inverting input, an inverting input, and an output, a current control coupled to the non-inverting input, which current control can supply a voltage within a first range to the non-inverting input, which first range is between a minimum voltage and a maximum voltage, a virtual ground coupled to the inverting input, which virtual ground has a ground voltage between the minimum voltage and the maximum voltage, and a load path selectively coupling the output of the current drive differential amplifier to the lead, wherein the load path comprises a sensing resistor located between the output of the current drive differential amplifier and the lead.

In some embodiments, at least one of the first and second current control modules includes a current sense differential amplifier having a sense non-inverting input, a sense inverting input, and a sense output. In some embodiments, the sense non-inverting input is connected via a first resistor having a first resistance to the load path between the sensing resistor and the output of the current drive differential amplifier. In some embodiments, the sense inverting input is connected via a second resistor having the first resistance to the load path between the sensing resistor and the lead. In some embodiments, the sense non-inverting input is connected to the virtual ground via a third resistor having a second resistance, and the sense inverting input is connected to the sense output via a fourth resistor having the second resistance. In some embodiments, the second resistance is at least twice the first resistance, and in some embodiments, the second resistance is at least ten times the first resistance.

In some embodiments, the implantable neurostimulator can include a voltage sensor that can measure a voltage drop across the sensing resistor. In some embodiments, the voltage drop across the sensing resistor is measured by determining a difference between the ground voltage and the output of the current sense differential amplifier. In some embodiments, the first control module can selectively source current to the lead and to selectively sink current from the lead. In some embodiments, the second control module can selectively source current to the lead and to selectively sink current from the lead.

In some embodiments, the virtual ground coupled to the inverting input of the current drive differential amplifier has a voltage at the inverting input that is equal to the ground voltage of the virtual ground when at least one of the first control module and the second control module is operating at a steady state. In some embodiments, the current drive differential amplifier can source current when the supplied voltage applied to the non-inverting input of the current drive differential amplifier is greater than the ground voltage of the virtual ground. In some embodiments, the current drive differential amplifier can sink current when the supplied voltage applied to the non-inverting input of the current drive differential amplifier is less than the ground voltage of the virtual ground.

One aspect of the present disclosure relates to a method of controlling circuitry of an implantable neurostimulator to selectively source or sink current to an implantable lead electrically coupled thereto having a plurality of electrodes positionable proximate to a target region within a patient's body for delivering electrical stimulation to the target region. The method includes identifying a desired operation of a first differential amplifier, which first differential amplifier is located within a hermetically sealed internal volume of a bio-compatible housing, and which first differential amplifier can selectively source current to a lead and to selectively sink current from the lead, generating a first control signal to cause the first differential amplifier to either source current to the lead or sink current from the lead, and providing the first control signal to the first differential amplifier.

In some embodiments of the method, generating the first control signal can include determining whether the desired operation of the first differential amplifier is: sourcing current to the lead; or sinking current from the lead. In some embodiments of the method, generating the first control signal can include determining whether to source current from the first differential amplifier or to selectively sink current to the first differential amplifier. In some embodiments of the method, generating the first control signal can include generating the first control signal to have a voltage greater than virtual ground voltage if it is determined to source current from the first differential amplifier. In some embodiments, generating the control signal further includes generating the first control signal to have a voltage less than virtual ground voltage if it is determined to sink current to the first differential amplifier.

In some embodiments, the method includes identifying a desired operation of a second differential amplifier, which second differential amplifier is located within a hermetically sealed internal volume of a bio-compatible housing, and which second differential amplifier can selectively source current to the lead and to selectively sink current from the lead. In some embodiments, the method can include generating a second control signal to cause the second differential amplifier to either source current to the lead or sink current from the lead, and in some embodiments, the method can include providing the second control signal to the second differential amplifier.

In some embodiments, when the first control signal causes the first differential amplifier to source current to the lead, the second signal is generated to cause the second differential amplifier to sink current from the lead. In some embodiments, when the first control signal causes the first differential amplifier to sink current from the lead, the second signal is generated to cause the second differential amplifier to source current to the lead. In some embodiments, the first differential amplifier can selectively source current to a first at least one of the plurality of electrodes of the lead and to selectively sink current from the first at least one of the plurality of electrodes of the lead, and the second differential amplifier can selectively source current to a second at least one of the plurality of electrodes of the lead and to selectively sink current from the second at least one of the plurality of electrodes of the lead.

In some embodiments, the first at least one of the plurality of electrodes of the lead and the second at least one of the plurality of electrodes of the lead are selected to complete a circuit through the target region within the patient's body. In some embodiments, the target region of the patient's body includes sacral tissue. In some embodiments, the first differential amplifier and the second differential amplifier can source current or sink current to generate one or several electrical pulses. In some embodiments, the one or several electrical pulses are generated according to a pulse program specifying a parameter of the electrical pulse. In some embodiments, the one or several electrical pulses can be monopolar, and in some embodiments, the one or several electrical pulses can be bipolar.

One aspect of the present disclosure relates to an implantable neurostimulator for delivering one or more electrical pulses to a target region within a patient's body with an implantable lead comprising a plurality of electrodes positionable proximate to the target region and electrically coupleable thereto. The implantable neurostimulator includes an ASIC-less current source/sink generator that can include a first differential amplifier that can selectively source current to the lead and to sink current from the lead, and a second differential amplifier that can selectively source current to the lead and to sink current from the lead. The Implantable neurostimulator includes a stimulation controller that can generate a first electrical signal to select one of current sourcing or sinking for the first differential amplifier and a second electrical signal to select the other of current sourcing or sinking for the second differential amplifier.

In some embodiments, the first differential amplifier includes an inverting input connected to a virtual ground and a non-inverting input connected to a first current command. In some embodiments, the second differential amplifier includes an inverting input connected to the virtual ground and a non-inverting input connected to a second current command. In some embodiments, the virtual ground supplies a first voltage to the inverting input of the first differential amplifier and supplies the first voltage to the inverting input of the second differential amplifier.

In some embodiments, the first current command supplies a second voltage greater than the supplied first voltage when selecting the first differential amplifier for current sourcing, and the first current command supplies a second voltage less than the supplied first voltage when selecting the first differential amplifier for current sinking. In some embodiments, the second current command supplies a third voltage greater than the supplied first voltage when selecting the second differential amplifier for current sourcing, and the second current command supplies a third voltage less than the supplied first voltage when selecting the second differential amplifier for current sinking.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

DETAILED DESCRIPTION OF THE INVENTION

Figure 1:
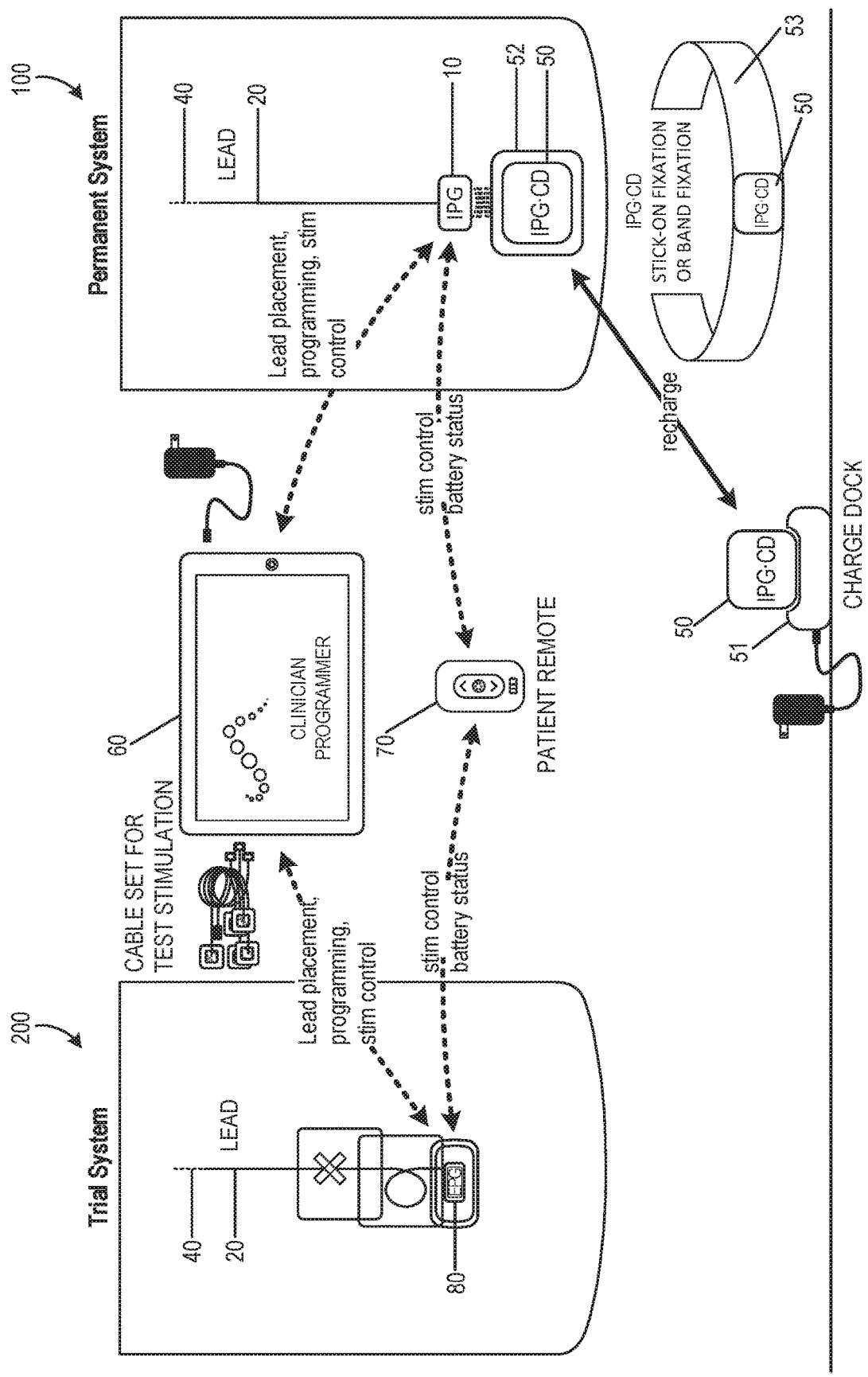
FIG. 1 schematically illustrates a nerve stimulation system, which includes a clinician programmer and a patient remote used in positioning and/or programming of both a trial neurostimulation system and a permanently implanted neurostimulation system, in accordance with aspects of the invention.

The present invention relates to neurostimulation treatment systems and associated devices, as well as methods of treatment, implantation/placement and configuration of such treatment systems. In one particular embodiment, the invention relates to sacral nerve stimulation treatment systems configured to treat overactive bladder ("OAB") and relieve symptoms of bladder related dysfunction. It will be appreciated however that the present invention may also be utilized for any variety of neuromodulation uses, such as fecal dysfunction, the treatment of pain or other indications, such as movement or affective disorders, as will be appreciated by one of skill in the art.

I. Neurostimulation Indications

Neurostimulation (or neuromodulation as may be used interchangeably hereunder) treatment systems, such as any of those described herein, can be used to treat a variety of ailments and associated symptoms, such as acute pain disorders, movement disorders, affective disorders, as well as bladder related dysfunction. Examples of pain disorders that may be treated by neurostimulation include failed back surgery syndrome, reflex sympathetic dystrophy or complex regional pain syndrome, causalgia, arachnoiditis, and peripheral neuropathy. Movement orders include muscle paralysis, tremor, dystonia and Parkinson's disease. Affective disorders include depressions, obsessive-compulsive disorder, cluster headache, Tourette syndrome and certain types of chronic pain. Bladder related dysfunctions include, but are not limited to, OAB, urge incontinence, urgency-frequency, and urinary retention. OAB can include urge incontinence and urgency-frequency alone or in combination. Urge incontinence is the involuntary loss or urine associated with a sudden, strong desire to void (urgency). Urgency-frequency is the frequent, often uncontrollable urges to urinate (urgency) that often result in voiding in very small amounts (frequency). Urinary retention is the inability to empty the bladder. Neurostimulation treatments can be configured to address a particular condition by effecting neurostimulation of targeted nerve tissues relating to the sensory and/or motor control associated with that condition or associated symptom.

In one aspect, the methods and systems described herein are particularly suited for treatment of urinary and fecal dysfunctions. These conditions have been historically underrecognized and significantly underserved by the medical community. OAB is one of the most common urinary dysfunctions. It is a complex condition characterized by the presence of bothersome urinary symptoms, including urgency, frequency, nocturia and urge incontinence. It is estimated that about 33 million Americans suffer from OAB. Of the adult population, about 30% of all men and 40% of all women live with OAB symptoms.

OAB symptoms can have a significant negative impact on the psychosocial functioning and the quality of life of patients. People with OAB often restrict activities and/or develop coping strategies. Furthermore, OAB imposes a significant financial burden on individuals, their families, and healthcare organizations. The prevalence of co-morbid conditions is also significantly higher for patients with OAB than in the general population. Co-morbidities may include falls and fractures, urinary tract infections, skin infections, vulvovaginitis, cardiovascular, and central nervous system pathologies. Chronic constipation, fecal incontinence, and overlapping chronic constipation occur more frequently in patients with OAB.

Conventional treatments of OAB generally include lifestyle modifications as a first course of action. Lifestyle modifications include eliminating bladder irritants (such as caffeine) from the diet, managing fluid intake, reducing weight, stopping smoking, and managing bowel regularity. Behavioral modifications include changing voiding habits (such as bladder training and delayed voiding), training pelvic floor muscles to improve strength and control of urethral sphincter, biofeedback and techniques for urge suppression. Medications are considered a second-line treatment for OAB. These include anti-cholinergic medications (oral, transdermal patch, and gel) and oral beta-3 adrenergic agonists. However, anti-cholinergics are frequently associated with bothersome, systemic side effects including dry mouth, constipation, urinary retention, blurred vision, somnolence, and confusion. Studies have found that more than 50% of patients stop using anti-cholinergic medications within 90 days due to a lack of benefit, adverse events, or cost.

When these approaches are unsuccessful, third-line treatment options suggested by the American Urological Association include intradetrusor (bladder smooth muscle) injections of Botulinum Toxin (BoNT-A), Percutaneous Tibial Nerve Stimulation (PTNS) and Sacral Nerve Stimulation (SNM). BoNT-A (Botox®) is administered via a series of intradetrusor injections under cystoscopic guidance, but repeat injections of Botox are generally required every 4 to 12 months to maintain effect and Botox may undesirably result in urinary retention. A number or randomized controlled studies have shown some efficacy of BoNT-A in OAB patients, but long-term safety and effectiveness of BoNT-A for OAB is largely unknown.

Alternative treatment methods, typically considered when the above approaches prove ineffective, is neurostimulation of nerves relating to the urinary system. Such neurostimulation methods include PTNS and SNM. PTNS therapy consists of weekly, 30-minute sessions over a period of 12 weeks, each session using electrical stimulation that is delivered from a hand-held stimulator to the sacral plexus via the tibial nerve. For patients who respond well and continue treatment, ongoing sessions, typically every 3-4 weeks, are needed to maintain symptom reduction. There is potential for declining efficacy if patients fail to adhere to the treatment schedule. Efficacy of PTNS has been demonstrated in a few randomized-controlled studies, however, long-term safety and effectiveness of PTNS is relatively unknown at this time.

II. Sacral Neuromodulation

SNM is an established therapy that provides a safe, effective, reversible, and long-lasting treatment option for the management of urge incontinence, urgency-frequency, and non-obstructive urinary retention. SNM therapy involves the use of mild electrical pulses to stimulate the sacral nerves located in the lower back. Electrodes are placed next to a sacral nerve, usually at the S3 level, by inserting the electrode leads into the corresponding foramen of the sacrum. The electrodes are inserted subcutaneously and are subsequently attached to an implantable pulse generator (IPG), also referred to herein as an "implantable neurostimulator" or a "neurostimulator." The safety and effectiveness of SNM for the treatment of OAB, including durability at five years for both urge incontinence and urgency-frequency patients, is supported by multiple studies and is well-documented. SNM has also been approved to treat chronic fecal incontinence in patients who have failed or are not candidates for more conservative treatments.

A. Implantation of Sacral Neuromodulation System

Currently, SNM qualification has a trial phase and is followed, if successful, by a permanent implant. The trial phase is a test stimulation period where the patient is allowed to evaluate whether the therapy is effective. Typically, there are two techniques that are utilized to perform the test stimulation. The first is an office-based procedure termed the Percutaneous Nerve Evaluation (PNE) and the other is a staged trial.

In the PNE, a foramen needle is typically used first to identify the optimal stimulation location, usually at the S3 level, and to evaluate the integrity of the sacral nerves. Motor and sensory responses are used to verify correct needle placement as described in Table 1 below. A temporary stimulation lead (a unipolar electrode) is then placed near the sacral nerve under local anesthesia. This procedure can be performed in an office setting without fluoroscopy. The temporary lead is then connected to an external pulse generator (EPG) taped onto the skin of the patient during the trial phase. The stimulation level can be adjusted to provide an optimal comfort level for the particular patient. The patient will monitor his or her voiding for 3 to 7 days to see if there is any symptom improvement. The advantage of the PNE is that it is an incision free procedure that can be performed in the physician's office using local anesthesia. The disadvantage is that the temporary lead is not securely anchored in place and has the propensity to migrate away from the nerve with physical activity and thereby cause failure of the therapy. If a patient fails this trial test, the physician may still recommend the staged trial as described below. If the PNE trial is positive, the temporary trial lead is removed and a permanent quadri-polar tined lead is implanted along with an IPG under general anesthesia.

Figure 3A:
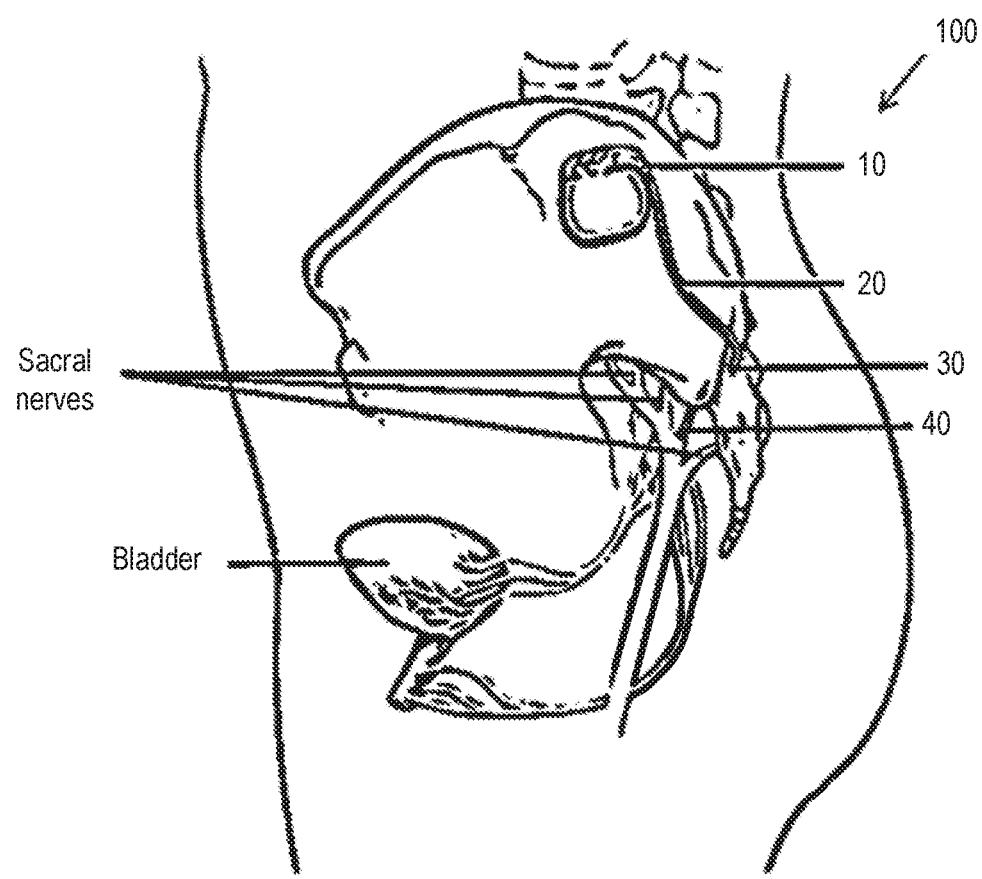
FIG. 3A shows an example of a fully implanted neurostimulation system in accordance with aspects of the invention.

A staged trial involves the implantation of the permanent quadri-polar tined stimulation lead into the patient from the start. It also requires the use of a foramen needle to identify the nerve and optimal stimulation location. The lead is implanted near the S3 sacral nerve and is connected to an EPG via a lead extension. This procedure is performed under fluoroscopic guidance in an operating room and under local or general anesthesia. The EPG is adjusted to provide an optimal comfort level for the patient and the patient monitors his or her voiding for up to two weeks. If the patient obtains meaningful symptom improvement, he or she is considered a suitable candidate for permanent implantation of the IPG under general anesthesia, typically in the upper buttock area, as shown in FIGS. 1 and 3A.

TABLE 1

Motor and Sensory Responses of SNM at Different Sacral Nerve Roots

| | Nerve Innervation | Response | | |
| --- | --- | --- | --- | --- |
| | | Pelvic Floor | Foot/calf/leg | Sensation |
| S2 | Primary somatic contributor of prudendal nerve for external sphincter, leg, foot | "clamp" of anal sphincter | Leg/hip rotation, plantar flexion of entire foot, contraction of calf | Contraction of base of penis, vagina |
| S3 | Virtually all pelvic autonomic functions and striated muscle (levator ani) | "bellows"** of perineum | Plantar flexion of great toe, occasionally other toes | Pulling in rectum, extending forward to scrotum or labia |

TABLE 1-continued

Motor and Sensory Responses of SNM at Different Sacral Nerve Roots

| | Nerve Innervation | Response | | |
|---|---|---|---|---|
| | | Pelvic Floor | Foot/calf/leg | Sensation |
| S4 | Pelvic autonomic and somatic No leg or foot | "bellows" | No lower extremity motor stimulation | Pulling in rectum only |

*Clamp: contraction of anal sphincter and, in males, retraction of base of penis. Move buttocks aside and look for anterior/posterior shortening of the perineal structures.
**Bellows: lifting and dropping of pelvic floor. Look for deepening and flattening of buttock groove.

In regard to measuring outcomes for SNM treatment of voiding dysfunction, the voiding dysfunction indications (e.g., urge incontinence, urgency-frequency, and non-obstructive urinary retention) are evaluated by unique primary voiding diary variables. The therapy outcomes are measured using these same variables. SNM therapy is considered successful if a minimum of 50% improvement occurs in any of primary voiding diary variables compared with the baseline. For urge incontinence patients, these voiding diary variables may include: number of leaking episodes per day, number of heavy leaking episodes per day, and number of pads used per day. For patients with urgency-frequency, primary voiding diary variables may include: number of voids per day, volume voided per void and degree of urgency experienced before each void. For patients with retention, primary voiding diary variables may include: catheterized volume per catheterization and number of catheterizations per day.

The mechanism of action of SNM is multifactorial and impacts the neuro-axis at several different levels. In patients with OAB, it is believed that pudendal afferents can activate the inhibitory reflexes that promote bladder storage by inhibiting the afferent limb of an abnormal voiding reflex. This blocks input to the pontine micturition center, thereby restricting involuntary detrusor contractions without interfering with normal voiding patterns. For patients with urinary retention, SNM is believed to activate the pudendal nerve afferents originating from the pelvic organs into the spinal cord. At the level of the spinal cord, pudendal afferents may turn on voiding reflexes by suppressing exaggerated guarding reflexes, thus relieving symptoms of patients with urinary retention so normal voiding can be facilitated. In patients with fecal incontinence, it is hypothesized that SNM stimulates pudendal afferent somatic fibers that inhibit colonic propulsive activity and activates the internal anal sphincter, which in turn improves the symptoms of fecal incontinence patients. The present invention relates to a system adapted to deliver neurostimulation to targeted nerve tissues in a manner that disrupt, inhibit, or prevent neural activity in the targeted nerve tissues so as to provide therapeutic effect in treatment of OAB or bladder related dysfunction. In one aspect, the system is adapted to provide therapeutic effect by neurostimulation without inducing motor control of the muscles associated with OAB or bladder related dysfunction by the delivered neurostimulation. In another aspect, the system is adapted to provide such therapeutic effect by delivery of sub-threshold neurostimulation below a threshold that induces paresthesia and/or neuromuscular response or to allow adjustment of neurostimulation to delivery therapy at sub-threshold levels.

B. Positioning Neurostimulation Leads with EMG

While conventional approaches have shown efficacy in treatment of bladder related dysfunction, there exists a need to improve positioning of the neurostimulation leads and consistency between the trial and permanent implantation positions of the lead. Neurostimulation relies on consistently delivering therapeutic stimulation from a pulse generator, via one or more neurostimulation electrodes, to particular nerves or targeted regions. The neurostimulation electrodes are provided on a distal end of an implantable lead that can be advanced through a tunnel formed in patient tissue. Implantable neurostimulation systems provide patients with great freedom and mobility, but it may be easier to adjust the neurostimulation electrodes of such systems before they are surgically implanted. It is desirable for the physician to confirm that the patient has desired motor and/or sensory responses before implanting an IPG. For at least some treatments (including treatments of at least some forms of urinary and/or fecal dysfunction), demonstrating appropriate motor responses may be highly beneficial for accurate and objective lead placement while the sensory response may not be required or not available (e.g., patient is under general anesthesia).

Placement and calibration of the neurostimulation electrodes and implantable leads sufficiently close to specific nerves can be beneficial for the efficacy of treatment. Accordingly, aspects and embodiments of the present disclosure are directed to aiding and refining the accuracy and precision of neurostimulation electrode placement. Further, aspects and embodiments of the present disclosure are directed to aiding and refining protocols for setting therapeutic treatment signal parameters for a stimulation program implemented through implanted neurostimulation electrodes.

Prior to implantation of the permanent device, patients may undergo an initial testing phase to estimate potential response to treatment. As discussed above, PNE may be done under local anesthesia, using a test needle to identify the appropriate sacral nerve(s) according to a subjective sensory response by the patient. Other testing procedures can involve a two-stage surgical procedure, where a quadripolar tined lead is implanted for a testing phase to determine if patients show a sufficient reduction in symptom frequency, and if appropriate, proceeding to the permanent surgical implantation of a neuromodulation device. For testing phases and permanent implantation, determining the location of lead placement can be dependent on subjective qualitative analysis by either or both of a patient or a physician.

In exemplary embodiments, determination of whether or not an implantable lead and neurostimulation electrode is located in a desired or correct location can be accomplished through use of electromyography ("EMG"), also known as surface electromyography. EMG, is a technique that uses an EMG system or module to evaluate and record electrical activity produced by muscles, producing a record called an electromyogram. EMG detects the electrical potential generated by muscle cells when those cells are electrically or neurologically activated. The signals can be analyzed to detect activation level or recruitment order. EMG can be performed through the skin surface of a patient, intramuscularly or through electrodes disposed within a patient near target muscles, or using a combination of external and internal structures. When a muscle or nerve is stimulated by an electrode, EMG can be used to determine if the related muscle is activated, (i.e. whether the muscle fully contracts, partially contracts, or does not contract) in response to the stimulus. Accordingly, the degree of activation of a muscle can indicate whether an implantable lead or neurostimulation electrode is located in the desired or correct location on a patient. Further, the degree of activation of a muscle can indicate whether a neurostimulation electrode is providing a stimulus of sufficient strength, amplitude, frequency, or duration to affect a treatment regimen on a patient. Thus, use of EMG provides an objective and quantitative means by which to standardize placement of implantable leads and neurostimulation electrodes, reducing the subjective assessment of patient sensory responses.

In some approaches, positional titration procedures may optionally be based in part on a paresthesia or pain-based subjective response from a patient. In contrast, EMG triggers a measurable and discrete muscular reaction. As the efficacy of treatment often relies on precise placement of the neurostimulation electrodes at target tissue locations and the consistent, repeatable delivery of neurostimulation therapy, using an objective EMG measurement can substantially improve the utility and success of SNM treatment. The measurable muscular reaction can be a partial or a complete muscular contraction, including a response below the triggering of an observable motor response, such as those shown in Table 1, depending on the stimulation of the target muscle. In addition, by utilizing a trial system that allows the neurostimulation lead to remain implanted for use in the permanently implanted system, the efficacy and outcome of the permanently implanted system is more consistent with the results of the trial period, which moreover leads to improved patient outcomes.

C. Example Embodiments

FIG. 1 schematically illustrates an exemplary nerve stimulation system, which includes both a trial neurostimulation system 200 and a permanently implanted neurostimulation system 100, in accordance with aspects of the invention. The FPG 80 and IPG 10 are each compatible with and wirelessly communicate with a clinician programmer 60 and a patient remote 70, which are used in positioning and/or programming the trial neurostimulation system 200 and/or permanently implanted system 100 after a successful trial. As discussed above, the clinician programmer can include specialized software, specialized hardware, and/or both, to aid in lead placement, programming, re-programming, stimulation control, and/or parameter setting. In addition, each of the IPG and the FPG allows the patient at least some control over stimulation (e.g., initiating a pre-set program, increasing or decreasing stimulation), and/or to monitor battery status with the patient remote. This approach also allows for an almost seamless transition between the trial system and the permanent system.

In one aspect, the clinician programmer 60 is used by a physician to adjust the settings of the EPG and/or IPG while the lead is implanted within the patient. The clinician programmer can be a tablet computer used by the clinician to program the IPG, or to control the EPG during the trial period. The clinician programmer can also include capability to record stimulation-induced electromyograms to facilitate lead placement and programming. The patient remote 70 can allow the patient to turn the stimulation on or of or to vary stimulation from the IPG while implanted, or from the EPG during the trial phase.

In another aspect, the clinician programmer 60 has a control unit which can include a microprocessor and specialized computer-code instructions for implementing methods and systems for use by a physician in deploying the treatment system and setting up treatment parameters. The clinician programmer generally includes a user interface which can be a graphical user interface, an EMG module, electrical contacts such as an EMG input that can couple to an EMG output stimulation cable, an EMG stimulation signal generator, and a stimulation power source. The stimulation cable can further be configured to couple to any or all of an access device (e.g., a foramen needle), a treatment lead of the system, or the like. The EMG input may be configured to be coupled with one or more sensory patch electrode(s) for attachment to the skin of the patient adjacent to a muscle (e.g., a muscle enervated by a target nerve). Other connectors of the clinician programmer may be configured for coupling with an electrical ground or ground patch, an electrical pulse generator (e.g., an EPG or an IPG), or the like. As noted above, the clinician programmer can include a module with hardware and computer-code to execute EMG analysis, where the module can be a component of the control unit microprocessor, a pre-processing unit coupled to or in-line with the stimulation and/or sensory cables, or the like.

In some aspects, the clinician programmer is configured to operate in combination with an EPG when placing leads in a patient body. The clinician programmer can be electronically coupled to the EPG during test simulation through a specialized cable set. The test simulation cable set can connect the clinician programmer device to the EPG and allow the clinician programmer to configure, modify, or otherwise program the electrodes on the leads connected to the EPG.

The electrical pulses generated by the EPG and IPG are delivered to one or more targeted nerves via one or more neurostimulation electrodes at or near a distal end of each of one or more leads. The leads can have a variety of shapes, can be a variety of sizes, and can be made from a variety of materials, which size, shape, and materials can be tailored to the specific treatment application. While in this embodiment, the lead is of a suitable size and length to extend from the IPG and through one of the foramen of the sacrum to a targeted sacral nerve, in various other applications, the leads may be, for example, implanted in a peripheral portion of the patient's body, such as in the arms or legs, and can be configured to deliver electrical pulses to the peripheral nerve such as may be used to relieve chronic pain. It is appreciated that the leads and/or the stimulation programs may vary according to the nerves being targeted.

Figure 2A:
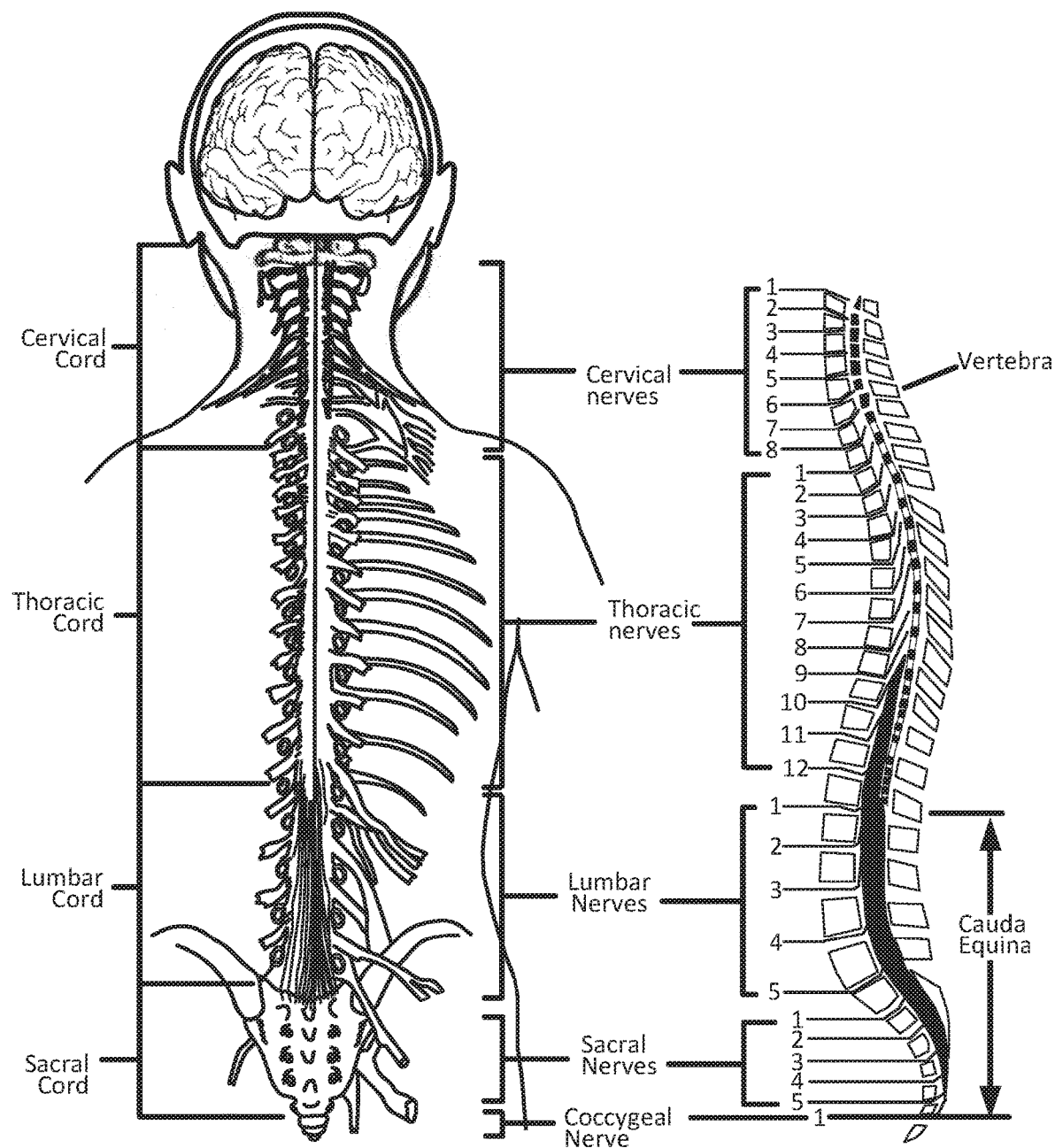
FIGS. 2A-2C show diagrams of the nerve structures along the spine, the lower back and sacrum region, which may be stimulated in accordance with aspects of the invention.
Figure 2B:
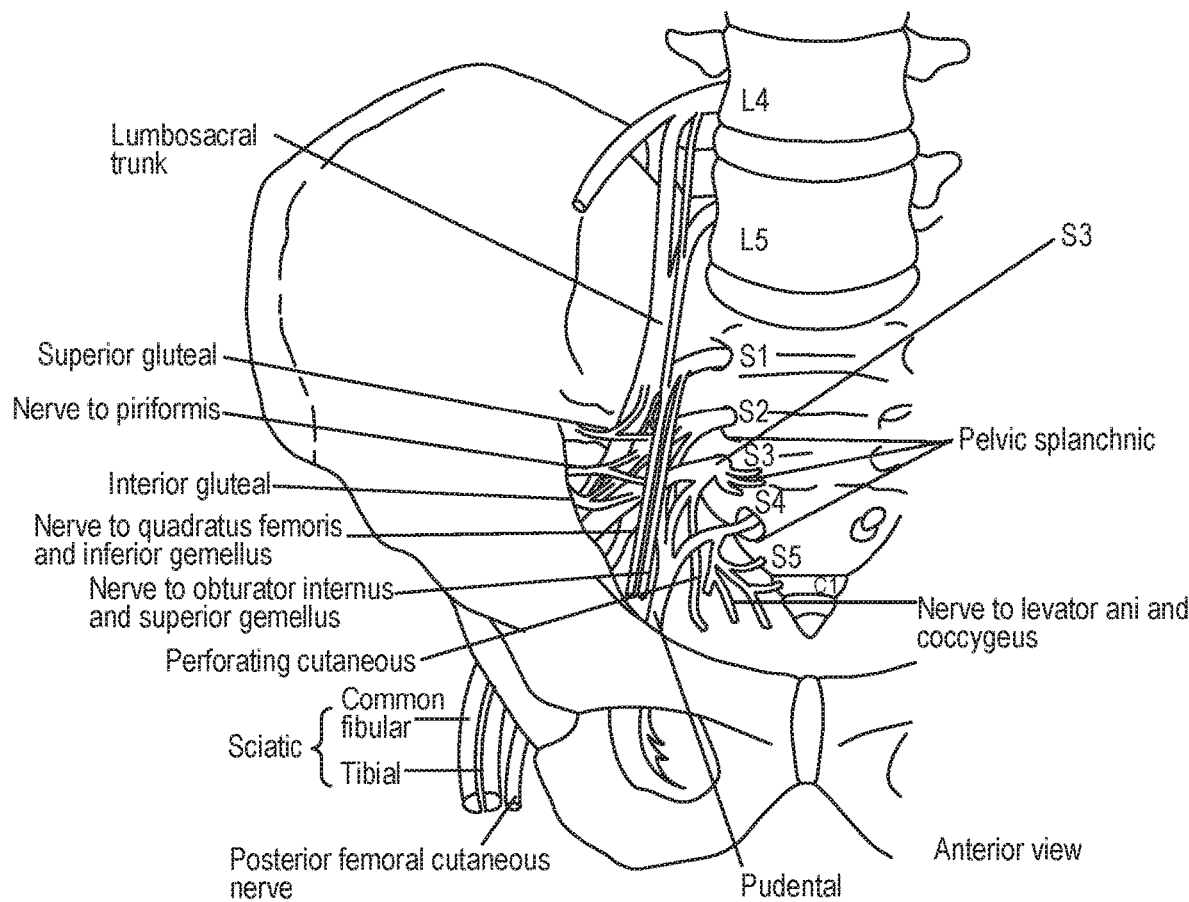
Figure 2C:
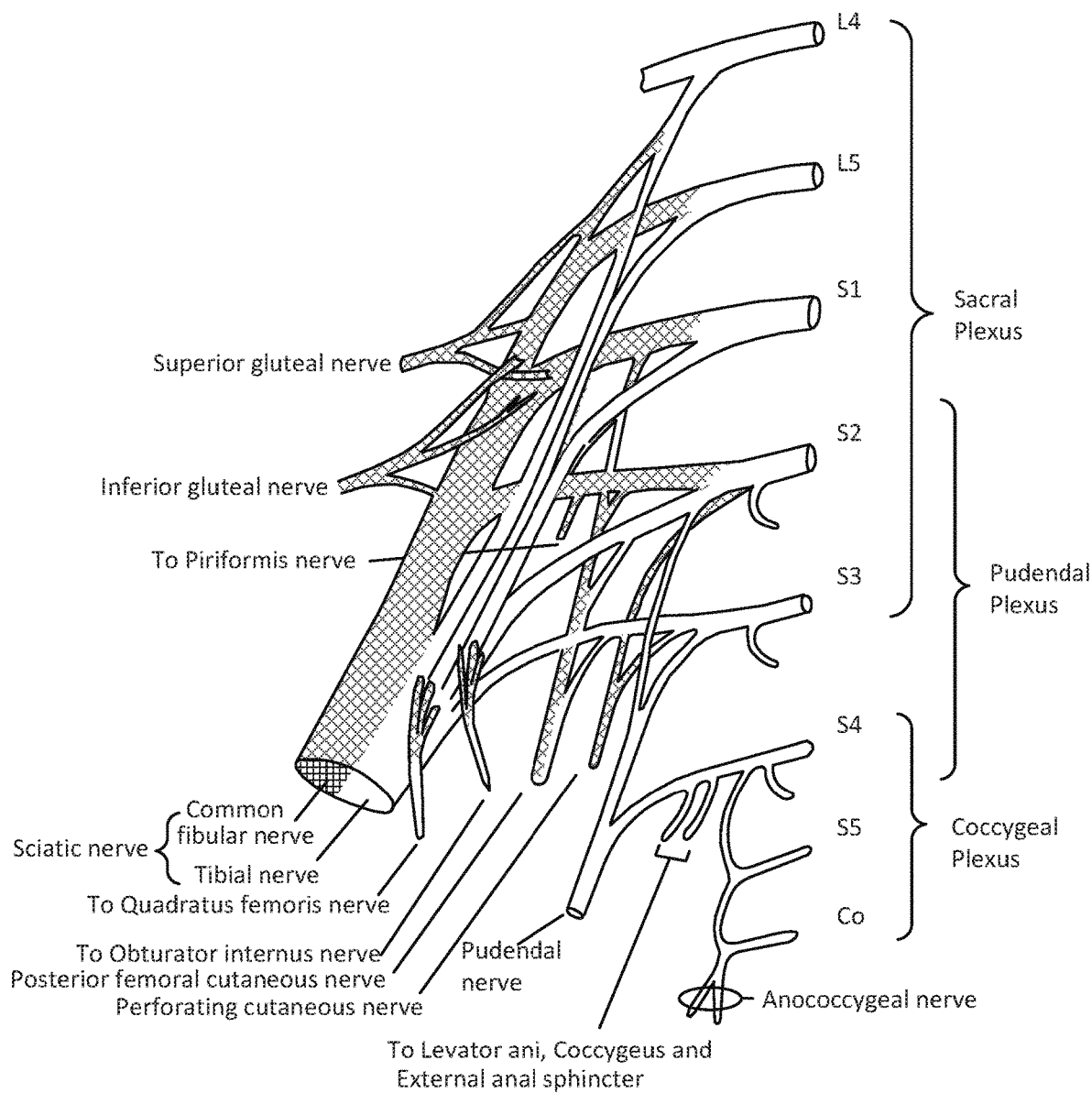

FIGS. 2A-2C show diagrams of various nerve structures of a patient, which may be used in neurostimulation treatments, in accordance with aspects of the invention. FIG. 2A shows the different sections of the spinal cord and the corresponding nerves within each section. The spinal cord is a long, thin bundle of nerves and support cells that extend from the brainstem along the cervical cord, through the thoracic cord and to the space between the first and second lumbar vertebra in the lumbar cord. Upon exiting the spinal cord, the nerve fibers split into multiple branches that innervate various muscles and organs transmitting impulses of sensation and control between the brain and the organs and muscles. Since certain nerves may include branches that innervate certain organs, such as the bladder, and branches that innervate certain muscles of the leg and foot, stimulation of the nerve at or near the nerve root near the spinal cord can stimulate the nerve branch that innervate the targeted organ, which may also result in muscle responses associated with the stimulation of the other nerve branch. Thus, by monitoring for certain muscle responses, such as those in Table 1, either visually, through the use of EMG as described herein or both, the physician can determine whether the targeted nerve is being stimulated. While stimulation at a certain threshold may trigger the noted muscle responses, stimulation at a sub-threshold level may still provide stimulation to the nerve associated with the targeted organ without causing the corresponding muscle response, and in some embodiments, without causing any paresthesia. This is advantageous as it allows for treatment of the condition by neurostimulation without otherwise causing patient discomfort, pain or undesired muscle responses.

FIG. 2B shows the nerves associated with the lower back section, in the lower lumbar cord region where the nerve bundles exit the spinal cord and travel through the sacral foramens of the sacrum. In some embodiments, the neurostimulation lead is advanced through the foramen until the neurostimulation electrodes are positioned at the anterior sacral nerve root, while the anchoring portion of the lead proximal of the stimulation electrodes are generally disposed dorsal of the sacral foramen through which the lead passes, so as to anchor the lead in position. FIG. 2C shows detail views of the nerves of the lumbosacral trunk and the sacral plexus, in particular, the S1-S5 nerves of the lower sacrum. The S3 sacral nerve is of particular interest for treatment of bladder related dysfunction, and in particular OAB.

FIG. 3A schematically illustrates an example of a fully implanted neurostimulation system 100 adapted for sacral nerve stimulation. Neurostimulation system 100 includes an IPG implanted in a lower back region and connected to a neurostimulation lead extending through the S3 foramen for stimulation of the S3 sacral nerve. The lead is anchored by a tined anchor portion 30 that maintains a position of a set of neurostimulation electrodes 40 along the targeted nerve, which in this example, is the anterior sacral nerve root S3 which enervates the bladder so as to provide therapy for various bladder related dysfunctions. While this embodiment is adapted for sacral nerve stimulation, it is appreciated that similar systems can be used in treating patients with, for example, chronic, severe, refractory neuropathic pain originating from peripheral nerves or various urinary dysfunctions or still further other indications. Implantable neurostimulation systems can be used to either stimulate a target peripheral nerve or the posterior epidural space of the spine.

Properties of the electrical pulses can be controlled via a controller of the implanted pulse generator. In some embodiments, these properties can include, for example, the frequency, strength, pattern, duration, or other aspects of the electrical pulses. These properties can include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In the embodiment depicted in FIG. 3A, the implantable neurostimulation system 100 includes a controller in the IPG having one or more pulse programs, plans, or patterns that may be pre-programmed or created as discussed above. In some embodiments, these same properties associated with the IPG may be used in an EPG of a partly implanted trial system used before implantation of the permanent neurostimulation system 100.

Figure 3B:
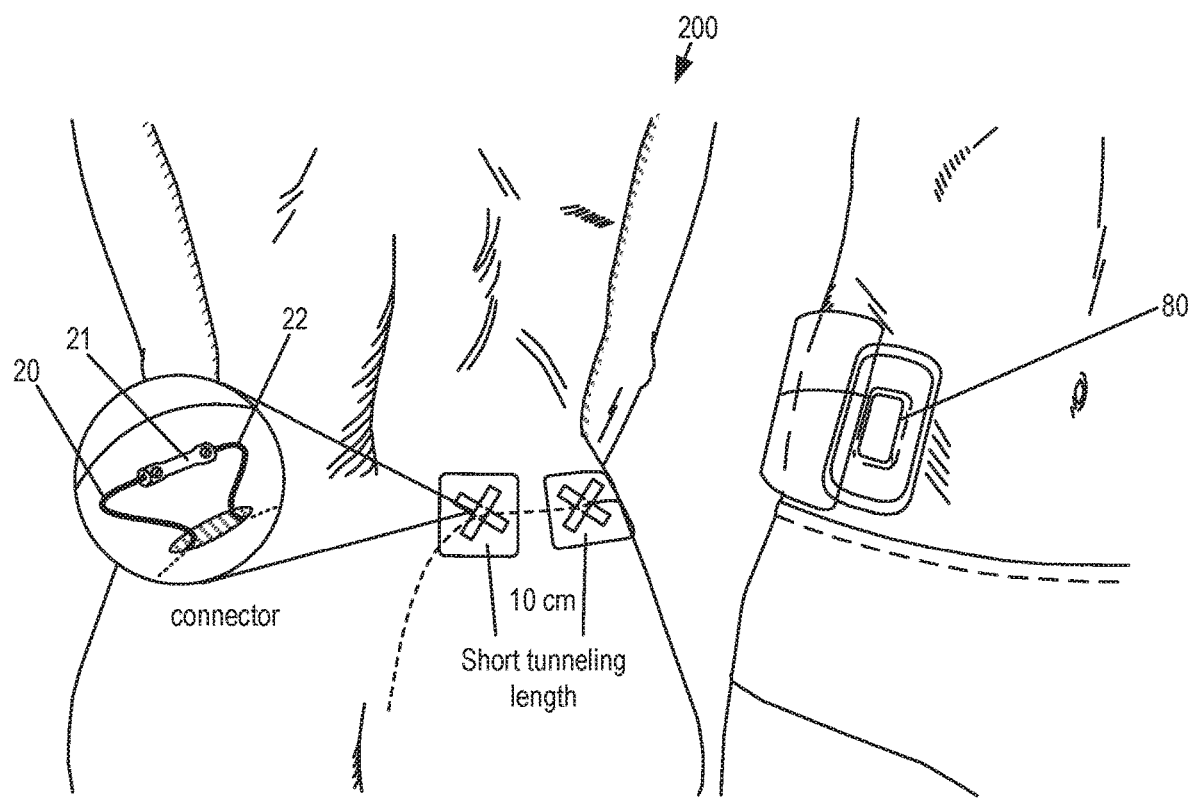
FIG. 3B shows an example of a neurostimulation system having a partly implanted stimulation lead and an external pulse generator adhered to the skin of the patient for use in a trial stimulation, in accordance with aspects of the invention.
Figure 3B:
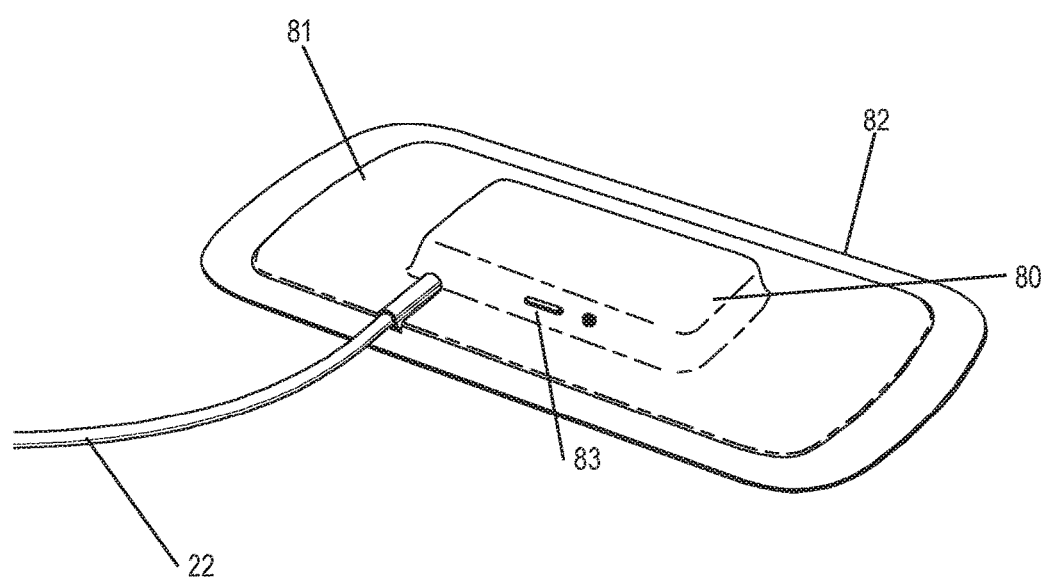

FIG. 3B shows a schematic illustration of a trial neurostimulation system 200 utilizing an EPG patch 81 adhered to the skin of a patient, particularly to the abdomen of a patient, the EPG 80 being encased within the patch. In one aspect, the lead is hardwired to the EPG, while in another the lead is removably coupled to the EPG through a port or aperture in the top surface of the flexible patch 81. Excess lead can be secured by an additional adherent patch. In one aspect, the EPG patch is disposable such that the lead can be disconnected and used in a permanently implanted system without removing the distal end of the lead from the target location. Alternatively, the entire system can be disposable and replaced with a permanent lead and IPG. When the lead of the trial system is implanted, an EMG obtained via the clinician programmer using one or more sensor patches can be used to ensure that the leads are placed at a location proximate to the target nerve or muscle, as discussed previously.

In some embodiments, the trial neurostimulation system utilizes an EPG 80 within an EPG patch 81 that is adhered to the skin of a patient and is coupled to the implanted neurostimulation lead 20 through a lead extension 22, which is coupled with the lead 20 through a connector 21. This extension and connector structure allows the lead to be extended so that the EPG patch can be placed on the abdomen and allows use of a lead having a length suitable for permanent implantation should the trial prove successful. This approach may utilize two percutaneous incisions, the connector provided in the first incision and the lead extensions extending through the second percutaneous incision, there being a short tunneling distance (e.g., about 10 cm) there between. This technique may also minimize movement of an implanted lead during conversion of the trial system to a permanently implanted system.

In one aspect, the EPG unit is wirelessly controlled by a patient remote and/or the clinician programmer in a similar or identical manner as the IPG of a permanently implanted system. The physician or patient may alter treatment provided by the EPG through use of such portable remotes or programmers and the treatments delivered are recorded on a memory of the programmer for use in determining a treatment suitable for use in a permanently implanted system. The clinician programmer can be used in lead placement, programming and/or stimulation control in each of the trial and permanent nerve stimulation systems. In addition, each nerve stimulation system allows the patient to control stimulation or monitor battery status with the patient remote. This configuration is advantageous as it allows for an almost seamless transition between the trial system and the permanent system. From the patient's viewpoint, the systems will operate in the same manner and be controlled in the same manner, such that the patient's subjective experience in using the trial system more closely matches what would be experienced in using the permanently implanted system. Thus, this configuration reduces any uncertainties the patient may have as to how the system will operate and be controlled such that the patient will be more likely to convert a trial system to a permanent system.

As shown in the detailed view of FIG. 3B, the EPG 80 is encased within a flexible laminated patch 81, which includes an aperture or port through which the EPG 80 is connected to the lead extension 22. The patch may further an "on/off"

button 83 with a molded tactile detail to allow the patient to turn the EPG on and/or off through the outside surface of the adherent patch 81. The underside of the patch 81 is covered with a skin-compatible adhesive 82 for continuous adhesion to a patient for the duration of the trial period. For example, a breathable strip having skin-compatible adhesive 82 would allow the EPG 80 to remain attached to the patient continuously during the trial, which may last over a week, typically two weeks to four weeks, or even longer.

Figure 4:
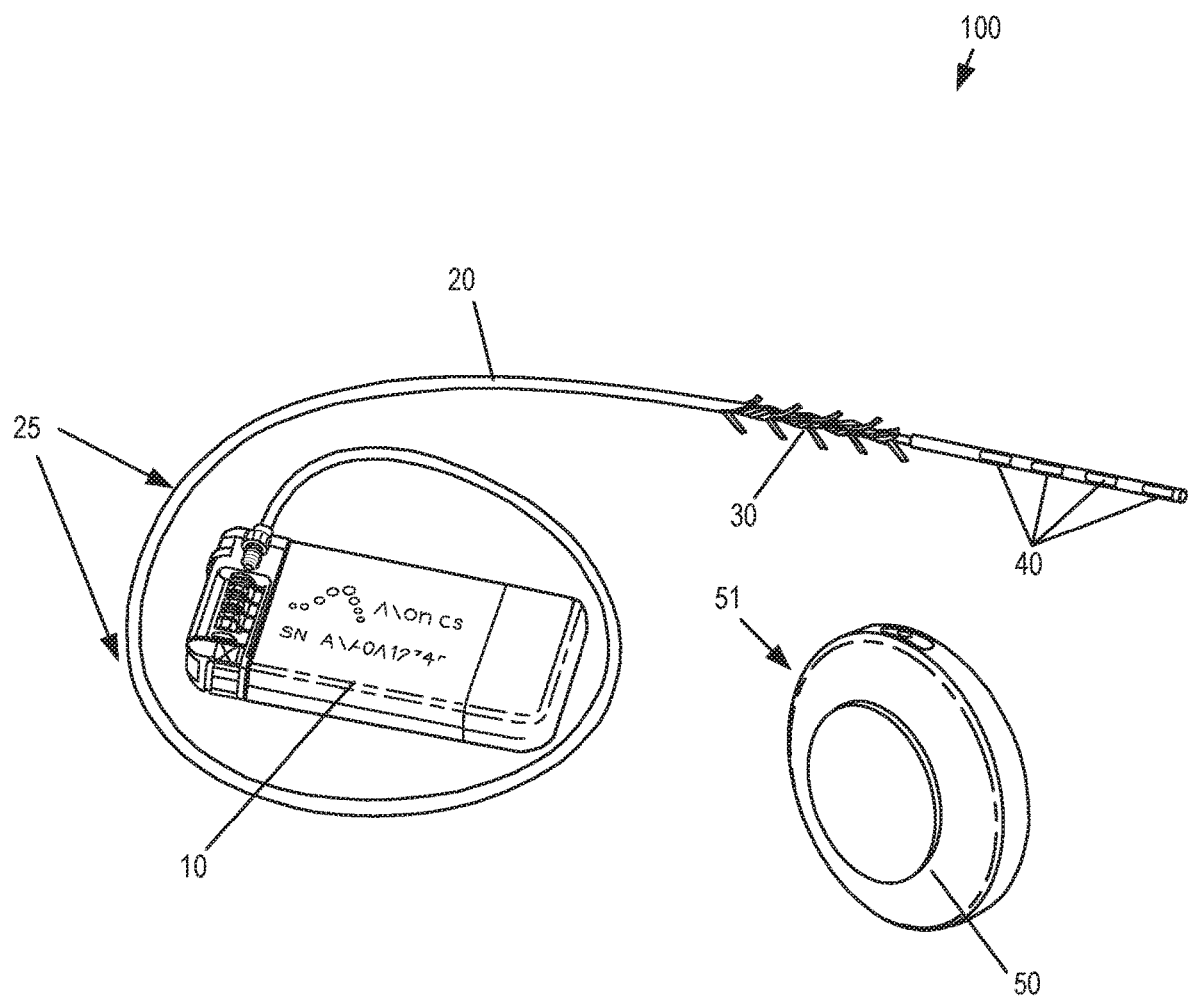
FIG. 4 shows an example of a neurostimulation system having an implantable stimulation lead, an implantable pulse generator, and an external charging device, in accordance with aspects of the invention.

FIG. 4 illustrates an example neurostimulation system 100 that is fully implantable and adapted for sacral nerve stimulation treatment. The implantable system 100 includes an IPG 10 that is coupled to a neurostimulation lead 20 that includes a group of neurostimulation electrodes 40 at a distal end of the lead. The lead includes a lead anchor portion 30 with a series of tines extending radially outward so as to anchor the lead and maintain a position of the neurostimulation lead 20 after implantation. The lead 20 may further include one or more radiopaque markers 25 to assist in locating and positioning the lead using visualization techniques such as fluoroscopy. In some embodiments, the IPG provides monopolar or bipolar electrical pulses that are delivered to the targeted nerves through one or more neurostimulation electrodes, typically four electrodes. In sacral nerve stimulation, the lead is typically implanted through the S3 foramen as described herein.

In one aspect, the IPG is rechargeable wirelessly through conductive coupling by use of a charging device 50 (CD), which is a portable device powered by a rechargeable battery to allow patient mobility while charging. The CD is used for transcutaneous charging of the IPG through RF induction. The CD can either be either patched to the patient's skin using an adhesive or can be held in place using a belt 53 or by an adhesive patch 52. The CD may be charged by plugging the CD directly into an outlet or by placing the CD in a charging dock or station 51 that connects to an AC wall outlet or other power source.

The system may further include a patient remote 70 and clinician programmer 60, each configured to wirelessly communicate with the implanted IPG, or with the FPG during a trial. The clinician programmer 60 may be a tablet computer used by the clinician to program the IPG and the FPG. The device also has the capability to record stimulation-induced electromyograms (EMGs) to facilitate lead placement, programming, and/or re-programming. The patient remote may be a battery-operated, portable device that utilizes radio-frequency (RF) signals to communicate with the FPG and IPG and allows the patient to adjust the stimulation levels, check the status of the IPG battery level, and/or to turn the stimulation on or off.

Figure 5A:
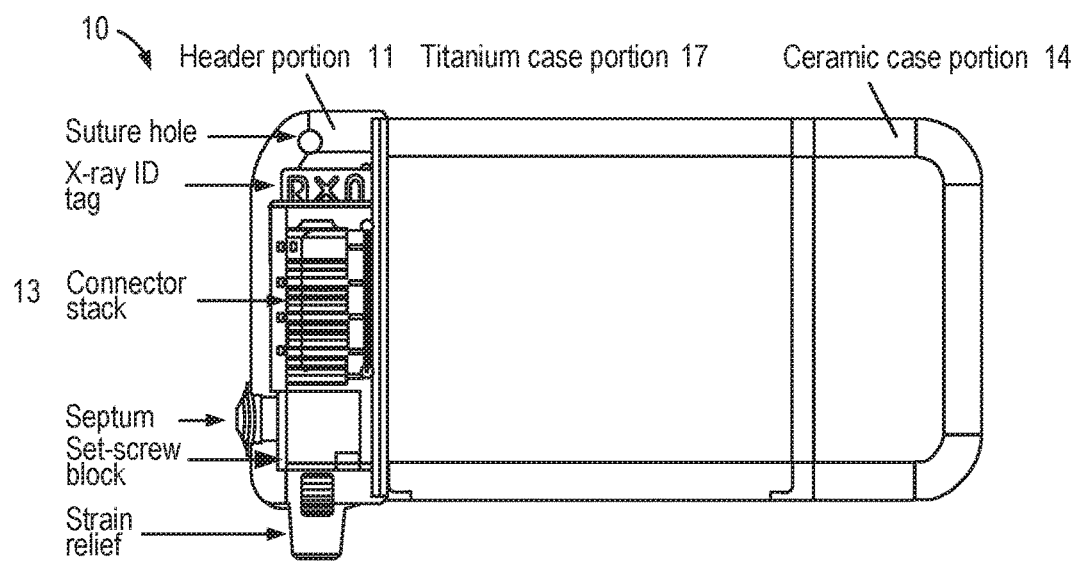
FIG. 5A-5C show detail views of an implantable pulse generator and associated components for use in a neurostimulation system, in accordance with aspects of the invention.
Figure 5B:
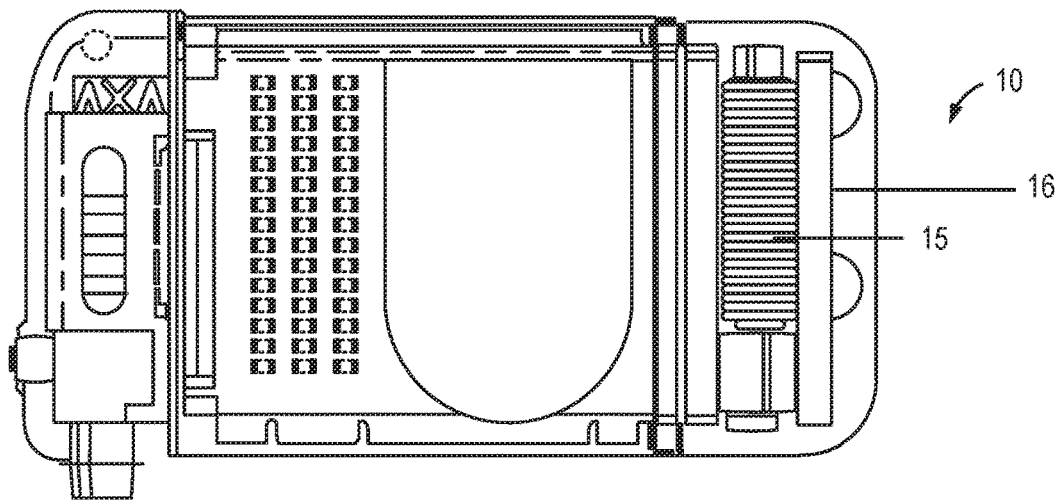
Figure 5C:
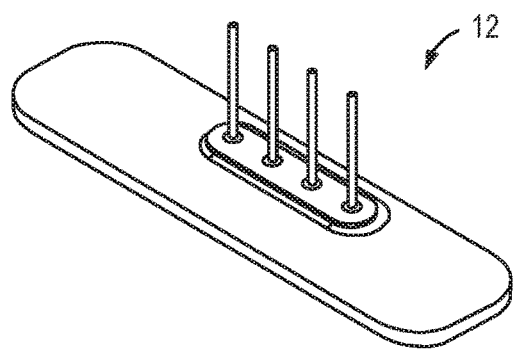

FIG. 5A-5C show detail views of the IPG and its internal components. In some embodiments, the pulse generator can generate one or more non-ablative electrical pulses that are delivered to a nerve to control pain or cause some other desired effect, for example to inhibit, prevent, or disrupt neural activity for the treatment of OAB or bladder related dysfunction. In some applications, the pulses having a pulse amplitude in a range between 0 mA to 1,000 mA, 0 mA to 100 mA, 0 mA to 50 mA, 0 mA to 25 mA, and/or any other or intermediate range of amplitudes may be used. One or more of the pulse generators can include a processor and/or memory adapted to provide instructions to and receive information from the other components of the implantable neurostimulation system. The processor can include a microprocessor, such as a commercially available microprocessor from Intel® or Advanced Micro Devices, Inc.®, or the like. An IPG may include an energy storage feature, such as one or more capacitors, and typically includes a wireless charging unit.

One or more properties of the electrical pulses can be controlled via a controller of the IPG or FPG. In some embodiments, these properties can include, for example, the frequency, strength, pattern, duration, or other aspects of the timing and magnitude of the electrical pulses. These properties can further include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In one aspect, the IPG 100 includes a controller having one or more pulse programs, plans, or patterns that may be created and/or pre-programmed. In some embodiments, the IPG can be programmed to vary stimulation parameters including pulse amplitude in a range from 0 mA to 10 mA, pulse width in a range from 50 μs to 500 μs, pulse frequency in a range from 5 Hz to 250 Hz, stimulation modes (e.g., continuous or cycling), and electrode configuration (e.g., anode, cathode, or off), to achieve the optimal therapeutic outcome specific to the patient. In particular, this allows for an optimal setting to be determined for each patient even though each parameter may vary from person to person.

As shown in FIGS. 5A-5B, the IPG may include a header portion 11 at one end and a ceramic portion 14 at the opposite end. The header portion 11 houses a feed through assembly 12 and connector stack 13, while the ceramic case portion 14 houses an antennae assembly 16 to facilitate wireless communication with the clinician program, the patient remote, and/or a charging coil to facilitate wireless charging with the CD. The remainder of the IPG is covered with a titanium case portion 17, which encases the printed circuit board, memory and controller components that facilitate the electrical pulse programs described above. In the example shown in FIG. 5C, the header portion of the IPG includes a four-pin feed-through assembly 12 that couples with the connector stack 13 in which the proximal end of the lead is coupled. The four pins correspond to the four electrodes of the neurostimulation lead. In some embodiments, a Balseal® connector block is electrically connected to four platinum/iridium alloy feed-through pins which are brazed to an alumina ceramic insulator plate along with a titanium alloy flange. This feed-through assembly is laser seam welded to a titanium-ceramic brazed case to form a complete hermetic housing for the electronics, which complete hermetic housing can define a sealed internal volume. In some embodiments, some or all of the pieces of the IPG 10 forming the hermetic housing can be biocompatible, and specifically, can have external surfaces made of biocompatible materials.

In some embodiment, such as that shown in FIG. 5A, the ceramic and titanium brazed case is utilized on one end of the IPG where the ferrite coil and PCB antenna assemblies are positioned. A reliable hermetic seal is provided via a ceramic-to-metal brazing technique. The zirconia ceramic may comprise a 3Y-TZP (3 mol percent Yttria-stabilized tetragonal Zirconia Polycrystals) ceramic, which has a high flexural strength and impact resistance and has been commercially utilized in a number of implantable medical technologies. It will be appreciated, however, that other ceramics or other suitable materials may be used for construction of the IPG, and that ceramic may be used to form additional portions of the case.

In one aspect, utilization of ceramic material provides an efficient, radio-frequency-transparent window for wireless communication with the external patient remote and clinician's programmer as the communication antenna is housed inside the hermetic ceramic case. This ceramic window has further facilitated miniaturization of the implant while maintaining an efficient, radio-frequency-transparent window for long term and reliable wireless communication between the IPG and external controllers, such as the patient remote and clinician programmer. The IPG's wireless communication is generally stable over the lifetime of the device, unlike prior art products where the communication antenna is placed in the header outside the hermetic case. The communication reliability of such prior art devices tends to degrade due to the change in dielectric constant of the header material in the human body over time.

In another aspect, the ferrite core is part of the charging coil assembly 15, shown in FIG. 5B, which is positioned inside the ceramic case 14. The ferrite core concentrates the magnetic field flux through the ceramic case as opposed to the metallic case portion 17. This configuration maximizes coupling efficiency, which reduces the required magnetic field and in turn reduces device heating during charging. In particular, because the magnetic field flux is oriented in a direction perpendicular to the smallest metallic cross section area, heating during charging is minimized. This configuration also allows the IPG to be effectively charged at depth of 3 cm with the CD, when positioned on a skin surface of the patient near the IPG and reduces re-charging time.

Figure 6:
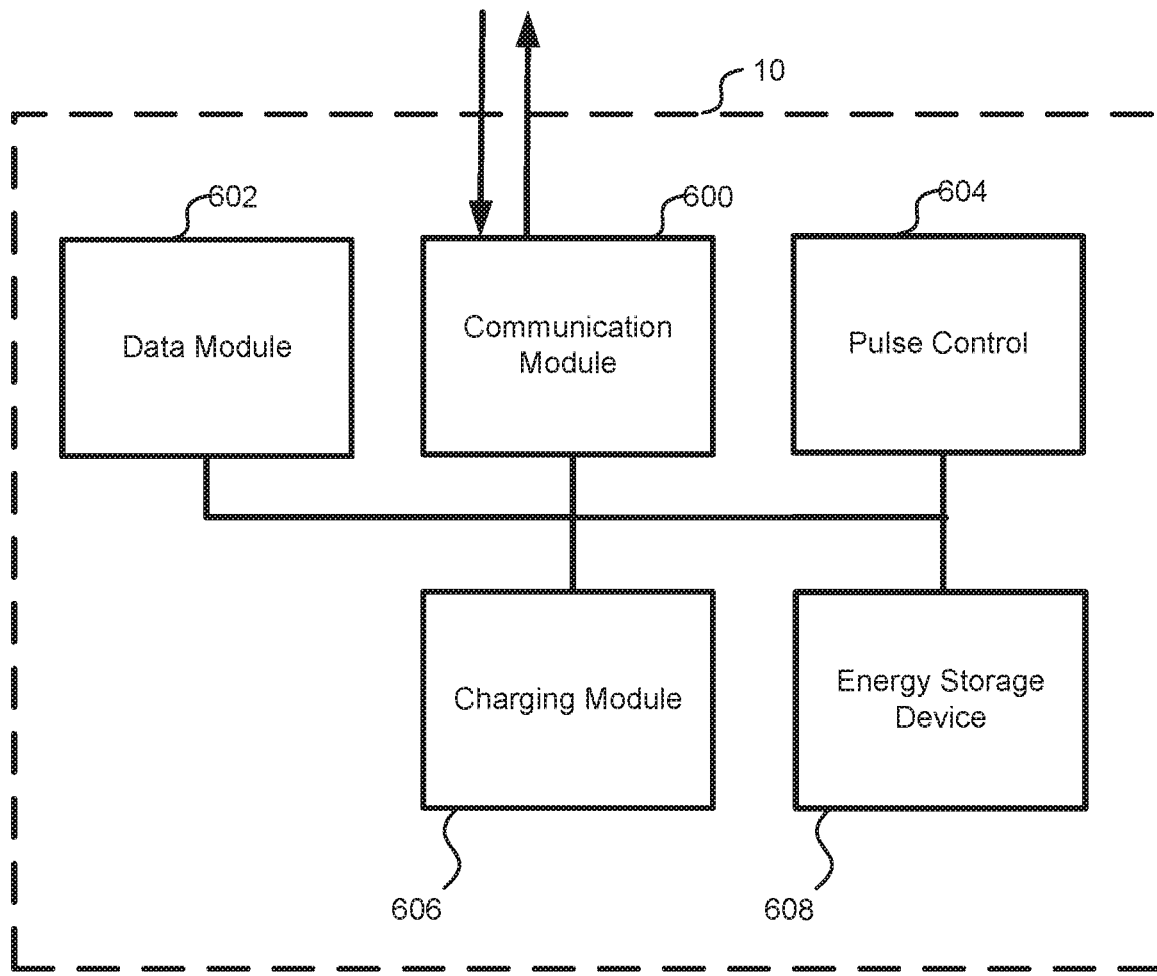
FIG. 6 shows a schematic illustration of one embodiment of the architecture of the IPG.

FIG. 6 shows a schematic illustration of one embodiment of the architecture of the IPG 10 is shown. The components forming the architecture of the IPG 10 can be embodied in hardware or software, and some or all of which components can be located within the hermetically sealed internal volume of the housing of the IPG 10. In some embodiments, each of the components of the architecture of the IPG 10 can be implemented using the processor, memory, and/or other hardware component of the IPG 10. In some embodiments, the components of the architecture of the IPG 10 can include software that interacts with the hardware of the IPG 10 to achieve a desired outcome.

In some embodiments, the IPG 10 can include, for example, a communication module 600. The communication module 600 can be configured to send data to and receive data from other components and/or devices of the exemplary nerve stimulation system including, for example, the clinician programmer 60 and/or the patient remote 70. In some embodiments, the communication module 600 can include one or several antennas and software configured to control the one or several antennas to send information to and receive information from one or several of the other components of the IPG 10.

The IPG 10 can further include a data module 602. The data module 602 can be configured to manage data relating to the identity and properties of the IPG 10. In some embodiments, the data module can include one or several database that can, for example, include information relating to the IPG 10 such as, for example, the identification of the IPG 10, one or several properties of the IPG 10, or the like. In one embodiment, the data identifying the IPG 10 can include, for example, a serial number of the IPG 10 and/or other identifier of the IPG 10 including, for example, a unique identifier of the IPG 10. In some embodiments, the information associated with the property of the IPG 10 can include, for example, data identifying the function of the IPG 10, data identifying the power consumption of the IPG 10, data identifying the charge capacity of the IPG 10 and/or power storage capacity of the IPG 10, data identifying potential and/or maximum rates of charging of the IPG 10, and/or the like.

The IPG 10 can include a pulse control 604. In some embodiments, the pulse control 604 can be configured to control the generation of one or several pulses by the IPG 10. In some embodiments, for example, this can be performed based on information that identifies one or several pulse patterns, programs, or the like. This information can further specify, for example, the frequency of pulses generated by the IPG 10, the duration of pulses generated by the IPG 10, the strength and/or magnitude of pulses generated by the IPG 10, or any other details relating to the creation of one or several pulses by the IPG 10. In some embodiments, this information can specify aspects of a pulse pattern and/or pulse program, such as, for example, the duration of the pulse pattern and/or pulse program, and/or the like. In some embodiments, information relating to and/or for controlling the pulse generation of the IPG 10 can be stored within the memory.

The IPG 10 can include a charging module 606. In some embodiments, the charging module 606 can be configured to control and/or monitor the charging/recharging of the IPG 10. In some embodiments, for example, the charging module 606 can include one or several features configured to receive energy for recharging the IPG 10 such as, for example, one or several inductive coils/features that can interact with one or several inductive coils/features of the charger 116 to create an inductive coupling to thereby recharge the IPG 10. In some embodiments, the charging module 606 can include hardware and/or software configured to monitor the charging of the IPG 10 including, for example, the charging coil assembly 15.

The IPG 10 can include an energy storage device 608. The energy storage device 608, which can include the energy storage features, can be any device configured to store energy and can include, for example, one or several batteries, capacitors, fuel cells, or the like. In some embodiments, the energy storage device 608 can be configured to receive charging energy from the charging module 606.

Figure 7:
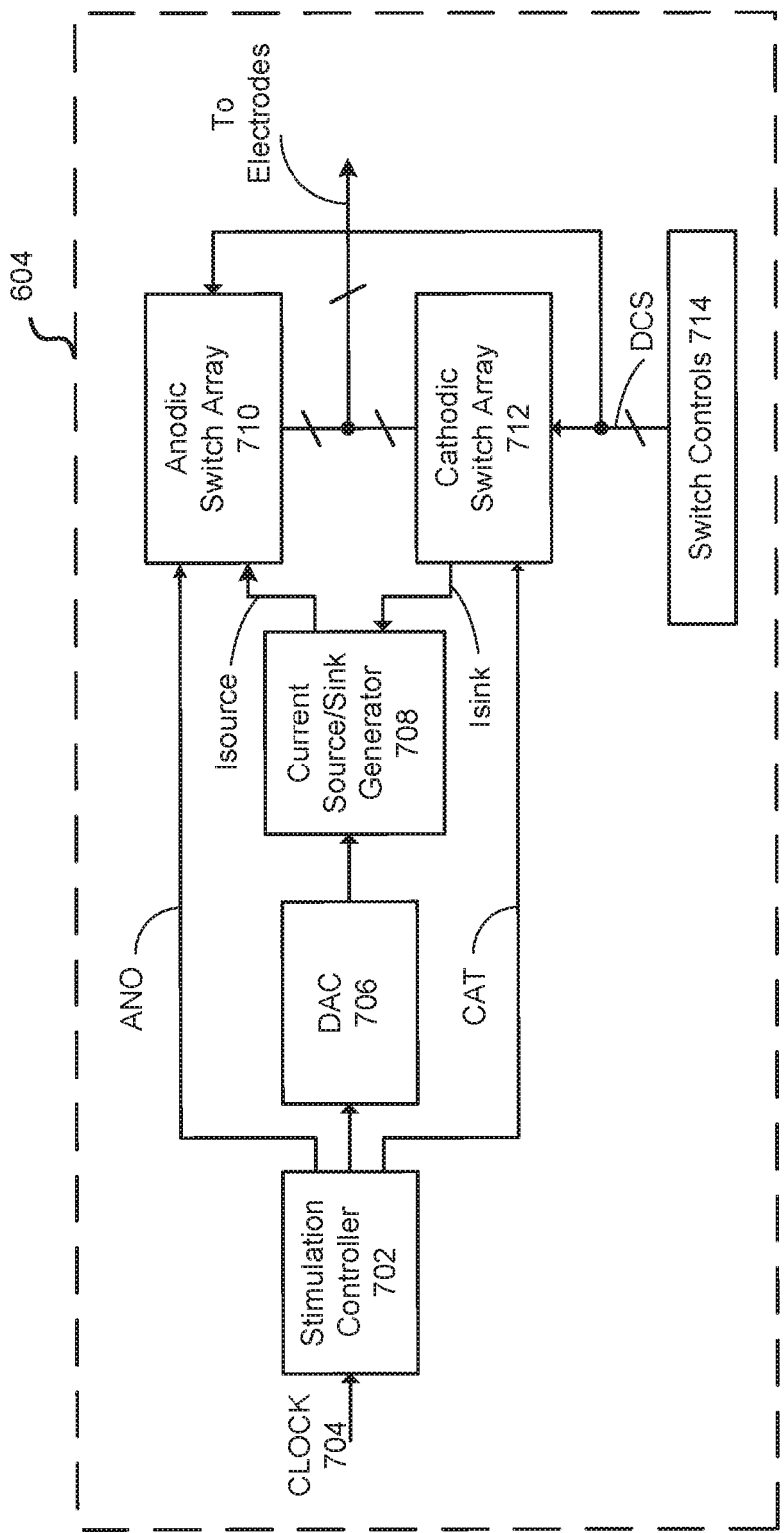
FIG. 7 shows a schematic illustration of one embodiment of the pulse control module.

FIG. 7 shows a schematic illustration of one embodiment of components of the pulse control module 604 having an ASICless current source/sink generator. The pulse control module 604 includes a stimulation controller 702, a digital to analog converter DAC 706, a current source/sink generator 708, an anodic switch array 710, a cathodic switch array 712, and switch controls 714. Although a single box depicting the current source sink generator 708 is shown, the current source sink generator 708 can comprises multiple circuits and/or components configured to selectively connect the current source/sink generator 708 to at least one of the leads to thereby allow the sourcing/sinking of current to or from the at least one of the leads. In some embodiments, the current source/sink generator 708 can comprise a plurality of current source/sinks including, for example, a first current source/sink and a second current source/sink, and in some embodiments, each of the anodic switch array 710 and the cathodic switch array 712 can comprise a plurality of switches.

The pulse control module 604 provides for the sourcing and sinking of current to one or several leads, and/or one or several electrodes on the leads. In some embodiments, this can include sourcing current to at least one lead and/or at least one electrode on at least one lead, and completing a circuit through the target tissue by sinking current from at least one lead and/or at least one electrode on at least one lead. In some embodiments, multiple currents can be sourced to one or several leads and/or electrodes, and similarly, in some embodiments, multiple currents can be sinked from one or several leads and/or electrodes. In some embodiments, the amount of sinked current can match the amount of sourced current.

The pulse control module 604 includes both an anodic switch array 710 and a cathodic switch array 712. The pulse control module 604 provides for selecting one or several electrodes for stimulation based upon tissue stimulation requirements determined by a clinician. This selection is made by a combination of the switch arrays 710, 712 and the switch controls 714. The outputs of the switch arrays 710, 712 are selected by setting the corresponding "bits" in switch controls 714. Switch controls 714 generate digital control signals DCS, which control the switching of switch arrays 710, 712 to select one or several electrodes for delivery of stimulation.

In some embodiments, the switch controls 714 can store information regarding stimulation pulse duration, amplitude and profile as well as other operational parameters. Based upon information stored in switch controls 714 and the CLOCK signal 704, stimulation controller 702 generates the desired stimulation pulse amplitude and triggers digital to analog converter DAC 706 to generate an output. Based upon the DAC 706 output, the current source/sink generator 708 provides a sink for $I_{sink}$ current and provides a source current $I_{source}$.

Figure 8:
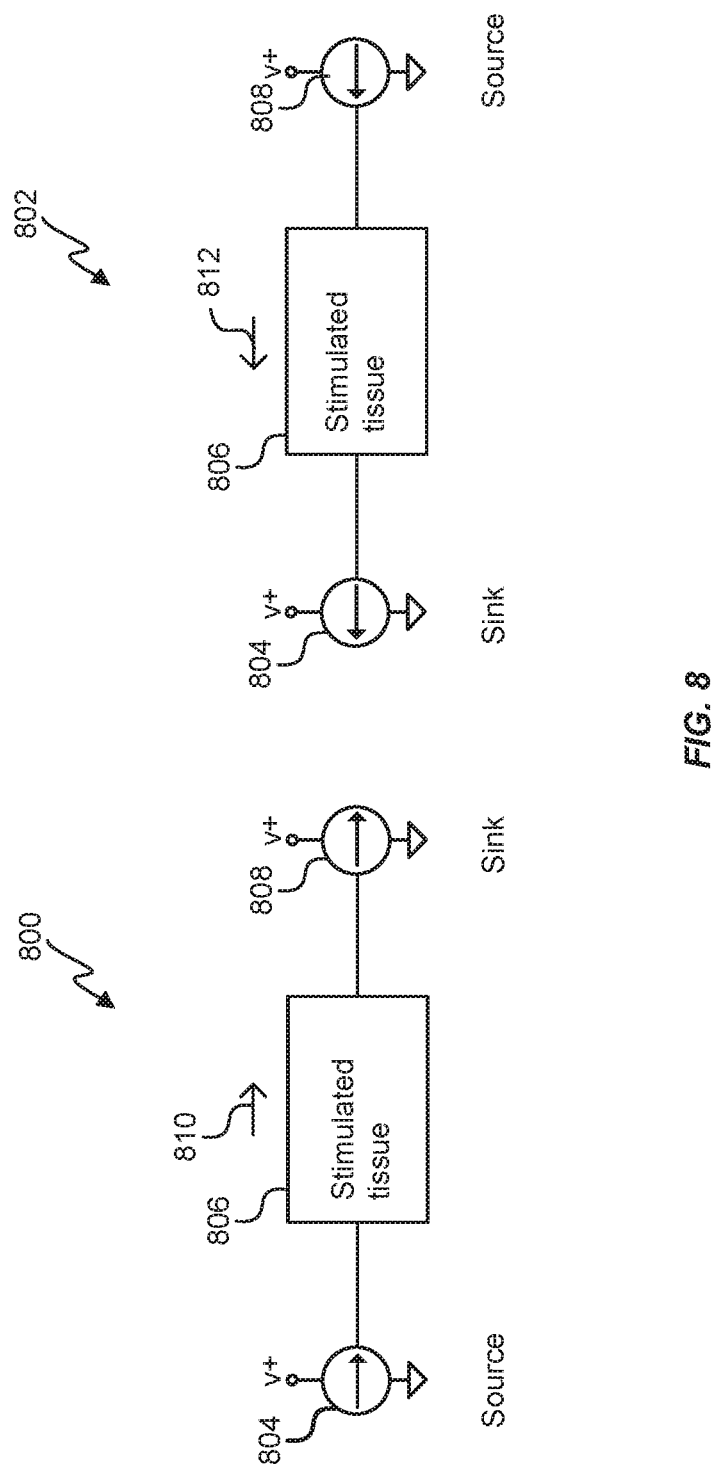
FIG. 8 shows a schematic illustration of embodiments of circuits created through target tissue with the IPG.

FIG. 8 shows a schematic illustration of a first circuit 800 and a second circuit 802 that can be created by a first current source/sink 804, tissue 806, and a second current source/sink 808. As seen in the first circuit 800, the first current source/sink 804 is configured for sourcing current, which sourced current passes through tissue 806, which tissue 806 can include the target tissue, as indicated by arrow 810 to the second current source/sink 808 which second current source/sink 808 is configured for current sinking in the first circuit 800.

In some embodiments, each of current source/sinks 804/808 can include circuitry configured for selectably sourcing or sinking current. Thus, the first current source/sink 804 can include first circuitry configured for selectable sourcing/sinking, and the second current source/sink can include second circuitry configured for selectable sourcing/sinking. In some embodiments, this circuitry can include a plurality of differential amplifiers, and in one embodiment, the first circuitry configured for selectable sourcing/sinking can include a first differential amplifier configured to selectively source/sink current, and the second circuitry configured for selectable sourcing/sinking can include a second differential amplifier configured to selectively source/sink current. Further, in some embodiments, each of the first and second circuitry configured for selectable sourcing/sinking can include a differential amplifier configured to generate an output related to the current provided to the target tissue. Thus, in some embodiments, the first circuitry configured for selectable sourcing/sinking can include a first sensing differential amplifier, and the second circuitry configured for selectable sourcing/sinking can include a second sensing differential amplifier.

As further seen in FIG. 8, in the second circuit 802, the second current source/sink 808 is configured for sourcing current, which sourced current passes through tissue 806 as indicated by arrow 812 to the first current source/sink 804, which first current source/sink 804 is configured for current sinking in the second circuit 802. Because the first and second source/sinks 804, 808 can each be selected to source current or to sink current, each of these components replaces both a current source and a current sink with a single component. This saves space and allows creation of smaller IPGs 10, and simplifies some aspects of circuit design.

Figure 9:
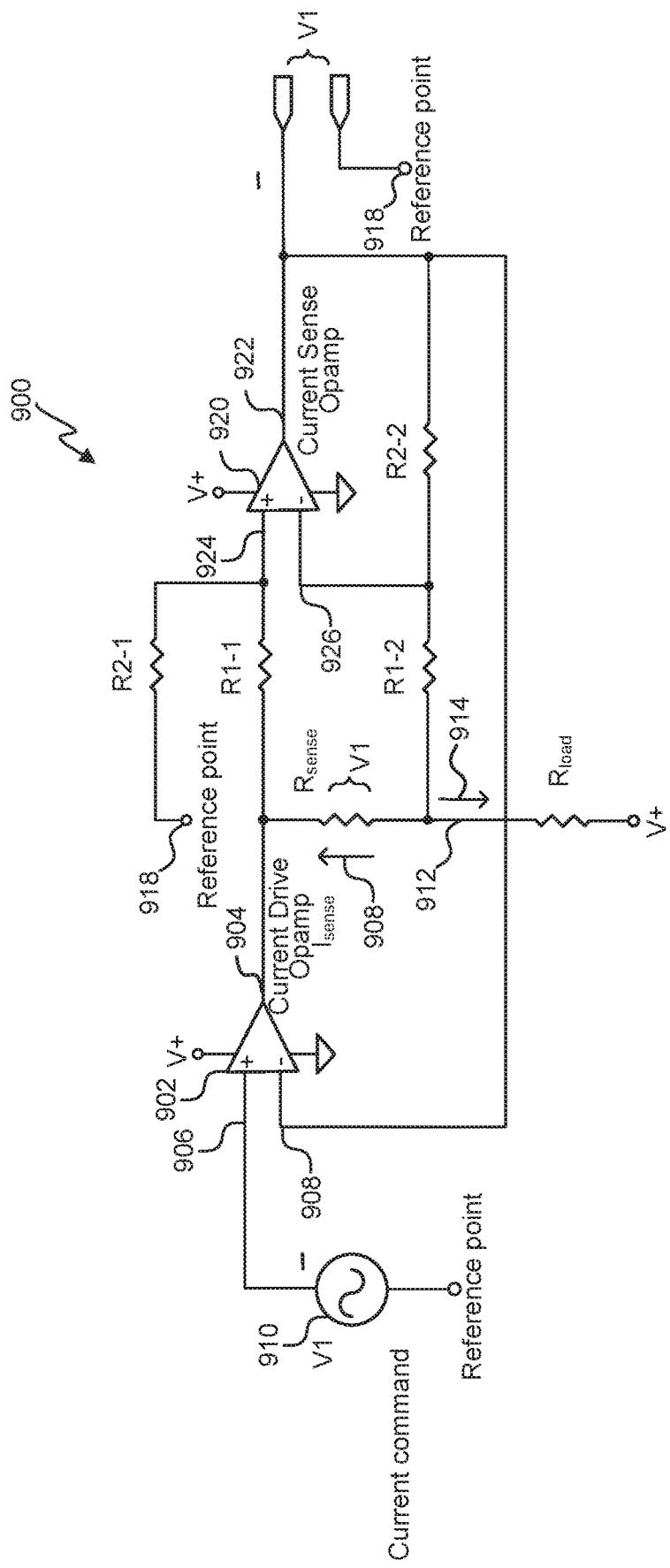
FIG. 9 a schematic illustration of one embodiment of a circuit creating a current source/sink.

FIG. 9 shows a schematic illustration of one embodiment of a current source/sink 900 which can be the same current source/sink used in one or both of the first current source/sink 804 and the second current source/sink 808. The current source/sink 900 depicted in FIG. 9 includes a current driver differential amplifier 902 that can be controlled to either source or sink current. This control can be accomplished by controlling one or both of the voltages at the inverting and non-inverting inputs of the current driver differential amplifier 902 such that the voltage applied to the non-inverting input is either greater than, equal to, or less than the voltage applied to the inverting input. In some embodiments, for example, the current source/sink 900 can be configured for current sourcing when the voltage applied to the non-inverting input of the current source/sink 900 is greater than the voltage applied to the inverting input of the current source/sink. Further, the current source/sink 900 can be configured for current sinking when the voltage applied to the non-inverting input of the current source/sink 900 is less than the voltage applied to the inverting input of the current source/sink 900. Additionally, the current source/sink can be configured for neither current sourcing nor sinking if the voltage applied to the non-inverting input of the current source/sink 900 is equal to the voltage applied to the inverting input.

In some embodiments, the current driver differential amplifier 902 can be configured to selectably source current or sink current by connecting one or of the inputs of the current driver differential amplifier 902 to a feature that can controllably apply a voltage within a range of voltages to that input. In one particular embodiment, one of the inputs of the current driver differential amplifier 902 is connected to a variable voltage supply, also referred to herein as a current command or a voltage command, and the other of the inputs is connected to a constant voltage supply referred to herein as a virtual ground. In such an embodiment, the current command can supply a voltage within a range of voltages to the input with which it is connected. Further, the voltage of the virtual ground can be selected to be between a maximum voltage and a minimum voltage defining the range of voltages supplyable to the input with which the current command is connected. In such a configuration, the current command can supply a voltage to the input to which it is connected that is less than, equal to, or greater than the voltage of the virtual ground applied to the other of the inputs of the current driver differential amplifier 902. Thus, by controlling the voltage supplied by the current command, the difference between the voltages applied to the inputs of the current driver differential amplifier 902 can be controlled, and the current driver differential amplifier 902 can be selected for sourcing, sinking, or non-operation.

In the embodiment of the current source/sink 900 of FIG. 9, the current source/sink 900 can include the current drive differential amplifier 902 configured to selectively source or sink current. The current drive differential amplifier 902 can include an output 904, an non-inverting input 906, and an inverting input 908. As depicted in FIG. 9, the non-inverting input 906 of the current drive differential amplifier 902 is connected to a current command 910. In some embodiments, current command 910 can be a component of the DAC 606, or alternatively can be the DAC 606.

The current command 910 can be configured to supply one or several voltages within a range of voltages to the non-inverting input 906 of the current drive differential amplifier 902. In some embodiments, the range of voltages can span from a minimum voltage to a maximum voltage. This range of voltages can be, for example, approximately 1V, 2V, 2.5V, 5V, 10V, 20V, 30V between 1V and 5V, between 5V and 10V, and/or any other or intermediate voltage. In some embodiments, the minimum voltage can be approximately 0V, 1V, 2V, 2.5V, 5V, 10V, 20V, and/or any other or intermediate voltage, and in some embodiments, the maximum voltage can be approximately 1V, 2V, 2.5V, 5V, 10V, 20V, 30V, and/or any other or intermediate voltage. As used herein, "approximately" or "substantially" refers to 1%, 5%, 10%, 15%, 20%, or 25% of the therewith associated value or range.

The output 904 of the current driver differential amplifier 902 is connected to an output path 912 which can be connected with the target tissue, represented by resistor $R_{load}$, via one of the switch arrays 710, 712. Current can flow through the output path in either a first direction as indicated by arrow 914 when the current drive differential amplifier 902 is selected for current sourcing, or in a second direction as indicated by arrow 916 when the current drive differential amplifier 902 is selected for current sinking.

As further indicated in FIG. 9, the inverting input 908 of the current driver differential amplifier 902 can be connected to the virtual ground 918. The virtual ground 918 can have a voltage that is within the range of voltages supplyable by the current command 910, and specifically can have a voltage that is between the minimum and the maximum voltages supplyable by the current command 910. The voltage of the virtual ground 918 can be, for example, approximately 1V, 2V, 2.5V, 5V, 10V, 20V, 30V, between 0V and 5V, between 5V and 10V, between 10V and 20V, and/or any other or intermediate value. In one particular embodiment, the current command 910 can supply a minimum voltage of approximately 0V and a maximum voltage of approximately 5V. In such an embodiment, the voltage of the virtual ground can be approximate 2.5V.

The connection of the inverting input 908 of the current driver differential amplifier 902 to the virtual ground 918 can be direct in that no components are located between the inverting input 908 of the current driver differential amplifier 902 and the virtual ground 918. Alternatively, the connection of the inverting input 908 of the current driver differential amplifier 902 to the virtual ground can be indirect in that components are located between the inverting input 908 of the current driver differential amplifier 902 and the virtual ground 918. The inverting input 908 of the current driver differential amplifier 902 can be indirectly connected to the virtual ground 918 such that the voltage supplied to the inverting input 908 is substantially equal to the voltage of the virtual ground 918. In some embodiments, the voltage supplied to the inverting input 908 is substantially equal to the voltage of the virtual ground 918 when the current source/sink 900 is operating at a steady-state.

The current, $I_{load}$ flowing through the target tissue, and being output by the current drive differential amplifier 902 can be monitored via high-side current sensing/monitoring. The high side current sensing/monitoring can be achieved via resistor $R_{sense}$ located in the output path 912 and a current sense differential amplifier 920 that generates an output voltage based on the voltage drop across $R_{sense}$. This output voltage from the current sense differential amplifier 920 can be compared to the virtual ground to determine the voltage drop across $R_{sense}$ by, for example, the stimulation controller. Based on the output voltage from the current sense differential amplifier 920, the current $I_{sense}$ passing through $R_{sense}$ of the output path 912 can be determined, which current $I_{sense}$ can be equal to, or approximately equal to current $I_{load}$.

The resistor $R_{sense}$ can have a resistance of approximately 1Ω, 2Ω, 5Ω, 7.5Ω, 10Ω, 12Ω, 15Ω, 20Ω, 30 MΩ, between 7.5Ω and 17.5Ω, between 9.5Ω and 14.5Ω, between 11Ω and 13Ω, and/or any other or intermediate resistance.

The current sense differential amplifier 920 has an output 922, a non-inverting input 924, and an inverting input 926. Both the non-inverting input 924 of the current sense differential amplifier 920 and the inverting input 926 of the current sense differential amplifier 920 connect to the output path 912. Specifically, the non-inverting input 924 of the current sense differential amplifier 920 connects to the output path 912 via resistor R1-1 before $R_{sense}$, and thus between the current drive differential amplifier 902 and $R_{sense}$, and the inverting input of the current sense differential amplifier 920 connects to the output path 912 via resistor R1-2 after $R_{sense}$. In some embodiments, the resistance of resistors R1-1 and R1-2 can be the same, and in some embodiments, these resistances can be different. In one embodiment the resistance of one or both of resistors R1-1 and R1-2 can be approximately 10 k•, 20 k•, 30 k•, 50 k•, 75 k•, 100 k•, 150 k•, 200 kΩ, between 50 kΩ and 150 kΩ, between 75 kΩ and 125 kΩ, between 90 kΩ and 110 kΩ, and/or any other or intermediate resistance. In some embodiments, the resistance of R1-1 and R1-2 can be selected to be significantly larger than the resistance of $R_{sense}$ so that an only insignificant amount of current flows through R1-1 and R1-2. In some particular embodiments, the resistances of R1-1 and R1-2 can be selected to be 2 times, 3 times, 4 times, 5 times, 10 times, 20 times, 50 times, 100 times, and/or any other or intermediate number of times larger than the resistance of $R_{sense}$.

As further seen in FIG. 9, the non-inverting input 924 of the current sense differential amplifier 920 is connected to the virtual ground 918 via resistor R2-1, and the inverting input 926 of the current sense differential amplifier 920 is connected to the output 922 of the current sense differential amplifier 920 via a resistor R2-2. In some embodiments, the resistance of resistors R2-1 and R2-2 can be the same, and in some embodiments, these resistances can be different. In one embodiment the resistance of one or both of resistors R2-1 and R2-2 can be approximately 100 kΩ, 200 kΩ, 500 kΩ, 750 kΩ, 1.0 MΩ, 1.2 MΩ, 1.5 MΩ, 2.0 MΩ, 3.0 MΩ, between 500 kΩ and 1.5 MΩ, between 750 kΩ and 1.25 MΩ, between 900 kΩ and 1.1 MΩ, and/or any other or intermediate resistance.

As further seen in FIG. 9, the output 922 of the current sense differential amplifier 920 is also connected to the inverting input 928 of the current sense differential amplifier 920 to create a feedback loop, and connected to the inverting input 908 of the current drive differential amplifier 902. Due to this feedback loop, the voltage output by the current sense differential amplifier 920 is equal to the voltage of the virtual ground 918 under at least some operating conditions such as, for example, steady-state operation. Accordingly, the voltage supplied to the inverting input 908 of the current driver differential amplifier 902 is equal to the voltage of the virtual ground 918 under at least some operating conditions.

Figure 10:
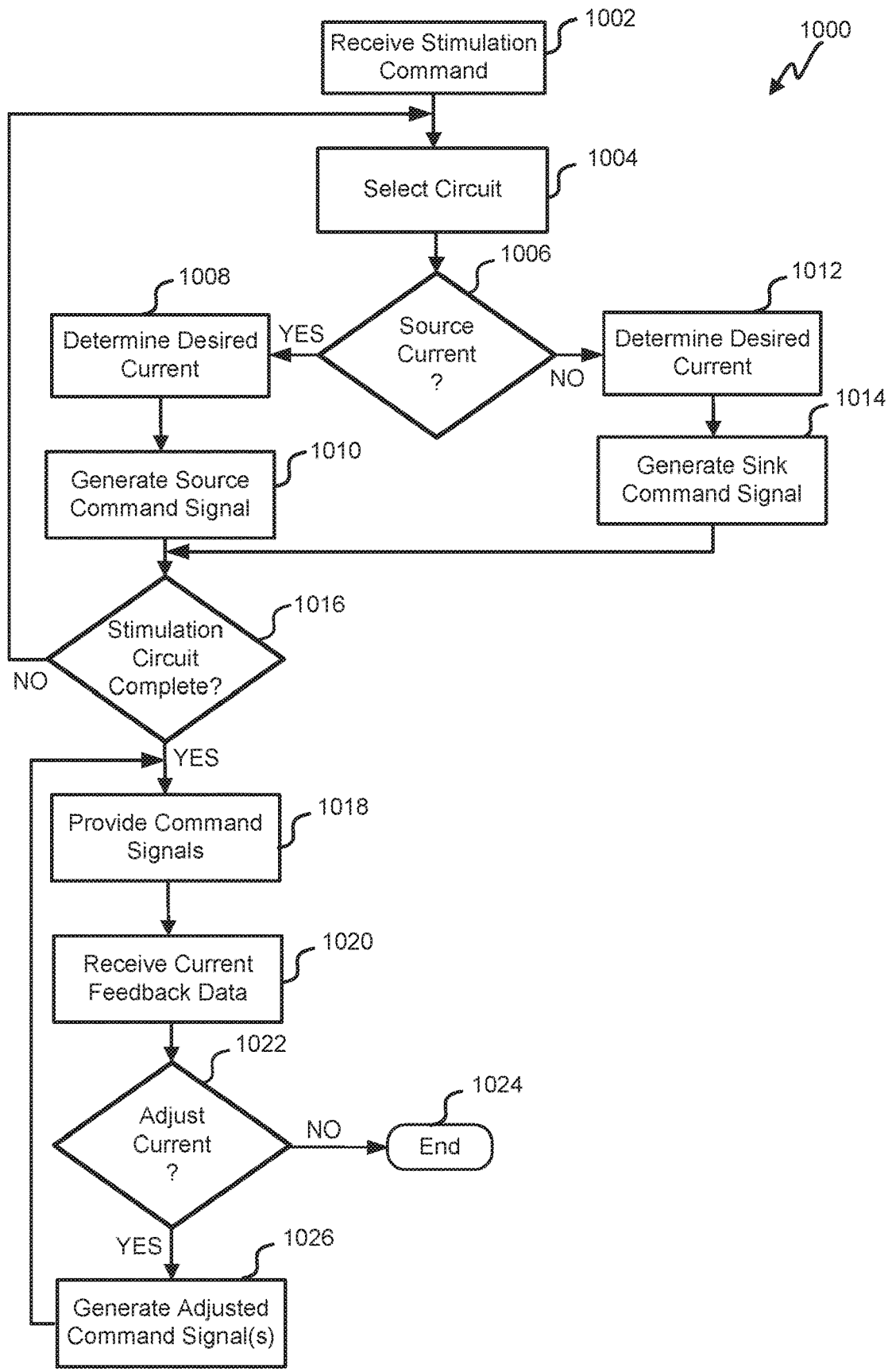
FIG. 10 is a flowchart illustrating one embodiment of a process for controlling current generation via one or several current sources/sinks.

FIG. 10 shows a flowchart illustrating one embodiment of a process 1000 for controlling the operation of an IPG 10, and specifically for generating one or several electrical pulses. The process 1000 can be performed with the IPG 10 disclosed herein, and can be specifically performed by the components disclosed in FIGS. 6-9. The process 1000 begins at block 1002, wherein a stimulation command is received. In some embodiments, the stimulation command can be received by the stimulation controller. The receipt of this command can, in some embodiments comprise the receipt of the CLOCK signal 904 by the stimulation controller 902.

After the stimulation command has been received, the process 1000 proceeds to block 1004, wherein a circuit is selected. In some embodiments, the selected circuit can be one or more of the current source/sinks 804, 808. In some embodiments, this step can include identifying some or all of the current source/sinks 804, 808 of the IPG 10, and selecting at least one of them. In some embodiments, this one of the current source/sinks 804, 808 can be selected to determine whether to designate this one of the current source/sinks 804, 808 for current sourcing or for current sinking.

After the circuit has been selected, the process 1000 proceeds to decision state 1006, wherein it is determined whether to source current from the selected one of the current source/sinks 804, 808. In some embodiments, this can include determining a desired direction of current flow through the target tissue and determining whether the selected circuit is best suited for sourcing or sinking to create this desired direction of current flow.

If it is determined that the selected circuit will source current, then the process 1000 proceeds to block 1008, wherein the desired current is determined. In some embodiments, this can include determining the desired amount of current sourced by the selected one of the current source/sinks 804, 808 and/or the amount of current desired to flow through the target tissue from the selected one of the current source/sinks 804, 808. In some embodiments, in which the selected one of the current source/sinks 804, 808 is desired for neither current sourcing nor sinking, this current amount can be zero. Alternatively, in some embodiments in which the selected one of the current source/sinks 804, 808 is selected for sourcing, the desired amount of current will be non-zero. In some embodiments, this determination can be made by, for example, the processor or the stimulation controller 902 according to the one or several pulse patterns, programs, or the like stored in the memory.

After the desired current has been determined, the process 1000 proceeds to block 1010, wherein the source command signal is generated. In some embodiments, the source command signal can be the signal provided to the selected one of the current source/sinks 804, 808, and specifically, can be the signal provided to the current sourcing differential amplifier 902, and more specifically to the non-inverting input 906 of the selected one of the current source/sinks 804, 808. This source command signal can be selected to supply a voltage to the selected one of the current source/sinks 804, 808, and specifically to the current sourcing differential amplifier 902 to select current sourcing Thus, in some embodiments, this command signal can supply a voltage to the non-inverting input 906 of the current drive differential amplifier 902 that is greater than the voltage supplied to the inverting input 908 of the current drive differential amplifier 902.

Returning again to decision state 1006, if it is determined not to source current at the selected one of the current source/sinks 804, 808, then the process 1000 proceeds to block 1012, wherein the desired current is determined. In some embodiments, this can include determining the desired amount of current sinked by the selected one of current source/sinks 804, 808 and/or the amount of current desired to flow through the target tissue. In some embodiments, in which the selected one of the current source/sinks 804, 808 is desired for neither current sourcing nor sinking, this current amount can be zero. Alternatively, in some embodiments in which the selected one of the current source/sinks 804, 808 is selected for sinking, the desired amount of current will be non-zero. In some embodiments, this determination can be made by, for example, the processor or the stimulation controller 902 according to the one or several pulse patterns, programs, or the like stored in the memory.

After the desired current has been determined, the process 1000 proceeds to block 1014, wherein the sink command signal is generated. In some embodiments, the sink command signal can be the signal provided to the selected one of the current source/sinks 804, 808, and specifically, can be the signal provided to the current drive differential amplifier 902, and more specifically to the non-inverting input 906 of the selected one of the current source/sinks 804, 808. This sink command signal can be selected to supply a voltage to the selected one of the current source/sinks 804, 808, and specifically to the current sourcing differential amplifier 902 to select current sinking. Thus, in some embodiments, this command signal can supply a voltage to the non-inverting input 906 of the current drive differential amplifier 902 that is less than the voltage supplied to the inverting input 908 of the current drive differential amplifier 902.

After the sink command signal has been generated, or returning again to block 1010, after the source command signal has been generated, the process 1000 proceeds to decision state 1016, wherein it is determined if the stimulation circuit is complete. In some embodiments, this can include determining whether at least one of the current source/sinks 804, 808 has been selected for current sourcing and whether at least one of the current source/sinks 804, 808 has been selected for sinking. This can also include determining whether the desired number of the current source/sinks 804, 808 have been selected for sourcing and sinking. In one particular embodiment, for example, multiples of the current source/sinks 804, 808 can be used for current sources and/or for current sinks. In such an embodiment, the determination of decision state 1016 can include determining whether the desired number of current source/sinks 804, 808 have been designated for each of sourcing and sinking, and if command signals have been generated for the same.

If it is determined that the stimulation circuit is not complete, then the process 1000 returns to block 1004. If it is determined that the stimulation circuit is complete, then the process 1000 proceeds to block 1018, wherein the command signals are provided to their associated current source/sinks 804, 808. After the command signals have been provided, the process 1000 proceeds to block 1020, wherein current feedback data is received. In some embodiments, this current feedback data can be based on the voltage drop across $R_{sense}$, and can indicate the amount of current passing through the target tissue, and specifically through each of the current source/sinks 804, 808 to the target tissue, or from the target tissue.

After the current feedback data has been received, the process 1000 proceeds to decision state 1022, wherein it is determined whether to adjust the current. In some embodiments, this can include the comparison of the current sourced or sinked by some or all of the current source/sinks 804, 808 to the desired amount of current. If no discrepancy between the desired current and the actual current is identified, then the process 1000 proceeds to block 1024 and ends, or alternatively, can return to block 1002 and continue with the receipt of a new stimulation command.

Returning again to decision state 1022, if a discrepancy between the desired current and the actual current is identified, then the process 1000 proceeds to block 1026, wherein one or several adjusted command signals are generated. In some embodiments, these can be command signals configured to bring the amount of actual current into closer alignment with the desired current. After these one or several adjusted command signals have been generated, the process 1000 returns to block 1018, and proceeds as outlined above.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A method of controlling circuitry of an implantable neurostimulator to selectively source or sink current to an implantable lead electrically coupled thereto comprising a plurality of electrodes positionable proximate to a target region within a patient's body for delivering electrical stimulation to the target region, the method comprising:
   identifying a desired operation of a first differential amplifier, wherein the first differential amplifier is located within a hermetically sealed internal volume of a bio-compatible housing of the implantable neurostimulator, and wherein the first differential amplifier is configured to selectively source current to a lead and to selectively sink current from the lead;
   generating a first control signal configured to cause the first differential amplifier to source current to the lead, wherein the first control signal comprises a voltage greater than a voltage of a constant voltage supply, wherein the constant voltage supply is coupled to an inverting input of the first differential amplifier; and
   providing the first control signal to a non-inverting input of the first differential amplifier with a first current command.

2. The method of claim 1, wherein the first differential amplifier comprises an inverting input connected to the constant voltage supply and a non-inverting input connected to the first current command, and wherein the first differential amplifier is configured to selectively source current to at least one of the plurality of electrodes sink current from at least one of the plurality of electrodes based on the voltage of the first control signal with respect to the constant voltage supply.

3. The method of claim 2, wherein generating the first control signal comprises determining whether to source current from the first differential amplifier or to selectively sink current to the first differential amplifier.

4. The method of claim 3, further comprising:
   receiving a first stimulation command;
   selecting a stimulation circuit, wherein the stimulation circuit comprises at least the first differential amplifier and a second differential amplifier, wherein the second differential amplifier is located within the hermetically sealed internal volume, wherein the second differential amplifier is configured to selectively source current to the lead and to selectively sink current from the lead, wherein the second differential amplifier comprises an inverting input connected to the constant voltage supply; and
   configuring the second differential amplifier to at least one of: source current to the lead; or sink current from the lead.

5. The method of claim 4, wherein the first differential amplifier is configured to selectively source current to a first at least one of the plurality of electrodes of the lead, and wherein the second differential amplifier is configured to selectively sink current from a second at least one of the plurality of electrodes of the lead.

6. The method of claim 5, wherein the first at least one of the plurality of electrodes of the lead and the second at least one of the plurality of electrodes of the lead are selected to complete a circuit through the target region within the patient's body, wherein the target region of the patient's body comprises sacral tissue.

7. The method of claim 4, further comprising:
   receiving a second stimulation command;
   selecting a second stimulation circuit, wherein the second stimulation circuit comprises at least the first differential amplifier and the second differential amplifier;
   generating a third control signal configured to cause the first differential amplifier to sink current from the lead, wherein the third control signal comprises a voltage less than the voltage of the constant voltage supply; and
   providing the third control signal to the first differential amplifier.

8. The method of claim 7, further comprising:
   generating a fourth control signal configured to cause the second differential amplifier to source current to the lead, wherein the fourth control signal comprises a voltage greater than the voltage of the constant voltage supply; and
   providing the fourth control signal to the second differential amplifier.

9. The method of claim 4, further comprising determining that the stimulation circuit is complete, wherein determining that the stimulation circuit is complete comprises determining at least one of: that a desired number of current sources have been selected; and that a desired number of current sinks have been selected.

10. The method of claim 4, further comprising determining that the stimulation circuit is incomplete, wherein determining that the stimulation circuit is incomplete comprises determining that less than a desired number of current sources and/or a desired number of current sinks have been selected.

11. The method of claim 10, further comprising:
    identifying a desired operation of an additional differential amplifier, wherein the additional differential amplifier is located within a hermetically sealed internal volume of a bio-compatible housing of the implantable neurostimulator, and wherein the additional differential amplifier is configured to selectively source current to a lead and to selectively sink current from the lead;
    generating an additional control signal configured to cause the additional differential amplifier to perform a desired one of: source current to the lead; or sink current from the lead; and
    providing the additional control signal to a non-inverting input of the additional differential amplifier.

12. The method of claim 4, further comprising receiving current feedback data indicating a measured current passing through the target region.

13. The method of claim 12, wherein the current feedback data is based on the output of at least one current sense differential amplifier.

14. The method of claim 13, wherein the at least one current sense differential amplifier generates a signal indicative of a voltage drop across at least one a sensing resistor.

15. The method of claim 14, wherein each of the first differential amplifier and the second differential amplifier can have unique current feedback data.

16. The method of claim 12, further comprising identifying a discrepancy between a desired current through the target region and the measured current through the target region.

17. The method of claim 16, further comprising adjusting the first control signal based on the identified discrepancy between the desired current and the measured current.

18. The method of claim 17, further comprising iteratively adjusting the first control signal until the discrepancy between the desired current and the measured current is eliminated.

19. The method of claim 4, wherein the first differential amplifier and the second differential amplifier are configured to source current or sink current to generate one or several electrical pulses.

20. The method of claim 19, wherein the one or several electrical pulses are generated according to a pulse program specifying a parameter of the one or several electrical pulses.

21. The method of claim 4, wherein the second differential amplifier comprises a non-inverting input connected to a second current command, and wherein configuring the second differential amplifier to at least one of: source current to the lead; or sink current from the lead comprises:
   generating a second control signal configured to cause the second differential amplifier to sink current from the lead, wherein the second control signal comprises a voltage less than the voltage of the constant voltage supply; and
   providing the second control signal to the second differential amplifier with the second current command.

* * * * *